(12) United States Patent
Woodard et al.

(10) Patent No.: US 11,439,412 B2
(45) Date of Patent: Sep. 13, 2022

(54) SCREW TARGETING GUIDE SYSTEM AND METHOD

(71) Applicant: Wright Medical Technology, Inc., Memphis, TN (US)

(72) Inventors: Joseph Ryan Woodard, Memphis, TN (US); Brian Robert Thoren, Memphis, TN (US); Paul Luttrell, Germantown, TN (US); Joel Vernois, Picquigny (FR); David Redfern, Hove (GB)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 119 days.

(21) Appl. No.: 16/500,501

(22) PCT Filed: Jul. 27, 2018

(86) PCT No.: PCT/US2018/044030
§ 371 (c)(1),
(2) Date: Oct. 3, 2019

(87) PCT Pub. No.: WO2019/027821
PCT Pub. Date: Feb. 7, 2019

(65) Prior Publication Data
US 2020/0060698 A1 Feb. 27, 2020

Related U.S. Application Data

(60) Provisional application No. 62/541,410, filed on Aug. 4, 2017.

(51) Int. Cl.
*A61B 17/17* (2006.01)
*A61B 17/56* (2006.01)

(52) U.S. Cl.
CPC ...... *A61B 17/1725* (2013.01); *A61B 17/1764* (2013.01); *A61B 17/1775* (2016.11);
(Continued)

(58) Field of Classification Search
CPC . A61B 17/17; A61B 17/1725; A61B 17/1764; A61B 17/1778; A61B 17/1775; A61B 17/1782
See application file for complete search history.

(56) References Cited

U.S. PATENT DOCUMENTS 6,210,415 B1 * 4/2001 Bester ................ A61B 17/1714
606/96
6,254,605 B1 7/2001 Howell
(Continued)

FOREIGN PATENT DOCUMENTS

JP 2008132324 A 6/2008
JP 2013511353 A 4/2013
(Continued)

OTHER PUBLICATIONS

First Examination Report issued in connection with corresponding Australian Patent Application No. 2018311839, dated Apr. 29, 2020, 4 pages.
(Continued)

*Primary Examiner* — Christopher J Beccia
(74) *Attorney, Agent, or Firm* — Duane Morris LLP

(57) ABSTRACT

A targeting guide includes a body defining a first guide hole sized and configured to receive a guide sleeve therethrough. The first guide hole extends through the body on a first axis. An alignment arm extends between a first end and a second end. The first end is coupled to the body. A tip extends from the second end of the alignment arm. A free end of the tip is aligned with the first axis of the first guide hole.

21 Claims, 22 Drawing Sheets

(52) U.S. Cl.
CPC ....... *A61B 17/1778* (2016.11); *A61B 17/1782* (2016.11); *A61B 2017/565* (2013.01)

(56) References Cited

U.S. PATENT DOCUMENTS

| | | | |
|---|---|---|---|
| 8,317,862 B2* | 11/2012 | Troger | A61B 17/1764 623/13.11 |
| 8,906,032 B2 | 12/2014 | Hanson et al. | |
| 8,986,315 B2 | 3/2015 | Durante et al. | |
| 9,186,163 B2* | 11/2015 | Cleveland | A61B 17/0485 |
| 9,687,260 B2 | 6/2017 | O'Reilly et al. | |
| 2003/0216742 A1 | 11/2003 | Wetzler et al. | |
| 2005/0177171 A1 | 8/2005 | Wetzler et al. | |
| 2008/0103506 A1 | 5/2008 | Volpi et al. | |
| 2009/0069816 A1* | 3/2009 | Sasing | A61B 17/1725 606/98 |
| 2009/0093813 A1 | 4/2009 | Elghazaly | |
| 2009/0099571 A1 | 4/2009 | Cresina et al. | |
| 2009/0306675 A1 | 12/2009 | Wong et al. | |
| 2011/0125160 A1* | 5/2011 | Bagga | A61B 17/1635 606/86 R |
| 2012/0330321 A1 | 12/2012 | Johnson et al. | |
| 2013/0030442 A1* | 1/2013 | Pilgeram | A61B 17/1764 606/96 |
| 2015/0150567 A1 | 6/2015 | Okuno et al. | |
| 2016/0030065 A1 | 2/2016 | Claes et al. | |
| 2017/0000537 A1* | 1/2017 | Fallin | A61B 17/68 |
| 2017/0042598 A1 | 2/2017 | Santrock et al. | |

FOREIGN PATENT DOCUMENTS

| | | |
|---|---|---|
| JP | 2013511353 A | 4/2014 |
| JP | 2014525770 A | 10/2014 |
| JP | 2015100451 A | 6/2015 |
| WO | WO2017031000 A1 | 2/2017 |
| WO | 2017040843 A1 | 3/2017 |
| WO | 2013180191 A1 | 12/2018 |

OTHER PUBLICATIONS

International Search Report and Written Opinion issued in connection with International Patent Application No. PCT/US2018/044030, 17 pages, dated Nov. 7, 2018.
Office Action issued in connection with Canadian Patent Application No. 3,059,253, 4 pages, dated Jan. 7, 2021.
Extended Search Report issued in connection with European Patent Application No. 18340538.5, 7 pages, dated Dec. 18, 2020.
Office Action issued in connection with Japanese Patent Application No. 2019-556341, 3 pages, dated Jan. 5, 2021.
Office Action issued in connection with Japanese Patent Application No. 2021-113626, dated Jul. 12, 2022, 4 pages.

* cited by examiner

//11,439,412 B2

SCREW TARGETING GUIDE SYSTEM AND METHOD

CROSS-REFERENCE TO RELATED APPLICATIONS

This application is a National Stage Application, filed under 35 U.S.C. 371, of International Patent Application No. PCT/US2018/044030, filed on Jul. 27, 2018 which claims benefit of U.S. Provisional Application Ser. No. 62/541,410, filed on Aug. 4, 2017, entitled "SCREW TARGETING GUIDE SYSTEM AND METHOD," the entire contents of which are incorporated herein by reference.

BACKGROUND

During surgery, such as foot surgery, it may be necessary to fix a position of a first bone fragment and a second bone fragment. For example, in some instances, an osteotomy is formed in a bone to correct one or more defects. After forming the osteotomy, a first fragment of the bone and a second fragment of a bone are positioned to correct the defect and are fixed in place using one or more fixation elements. In other embodiments, one or more bone fragments are formed as a result of an injury and/or medical procedure.

Current systems rely on the placement of guide elements prior to insertion of the fixation elements. Placement of the guide elements is performed by a surgeon and often requires the surgeon to insert and remove the guide element several times before a desired placement is achieved. The repeated insertion and removal of guide elements results in additional wounds in a patient and increased pain, recovery time, and complexity of surgery (including difficulty, increased surgical time, etc.)

SUMMARY

In various embodiments, a targeting guide for positioning guide elements is disclosed. The targeting guide includes a body defining a first guide hole sized and configured to receive a guide sleeve therethrough. The first guide hole extends through the body on a first axis. An alignment arm extends between a first end and a second end. The first end is coupled to the body. A tip extends from the second end of the alignment arm. A free end of the tip is aligned with the first axis of the first guide hole.

In various embodiments, a system is disclosed. The system includes a targeting guide having a body defining a first guide hole. The first guide hole extends through the body on a first axis. An alignment arm extends between a first end and a second end. The first end is coupled to the body. A tip extends from the second end of the alignment arm. A free end of the tip is aligned with the first axis of the first guide hole. A first sleeve sized and configured for insertion through the first guide hole. The first sleeve defines a channel extending therethrough.

In various embodiments, a method of fixing a first bone fragment and a second bone fragment is disclosed. The method includes positioning a targeting guide adjacent to a first bone. The targeting guide includes a body, an alignment arm extending between a first end coupled to the body and a second end, and a tip extending from the second end of the alignment arm and having a free end. A first sleeve is inserted through a first guide hole formed in the body. The first sleeve defines a first channel extending therethrough. A first guide element is inserted through the channel of the first sleeve and into the first bone. A portion of the tip of the targeting guide corresponds to an exit position of the first guide element from the first bone.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
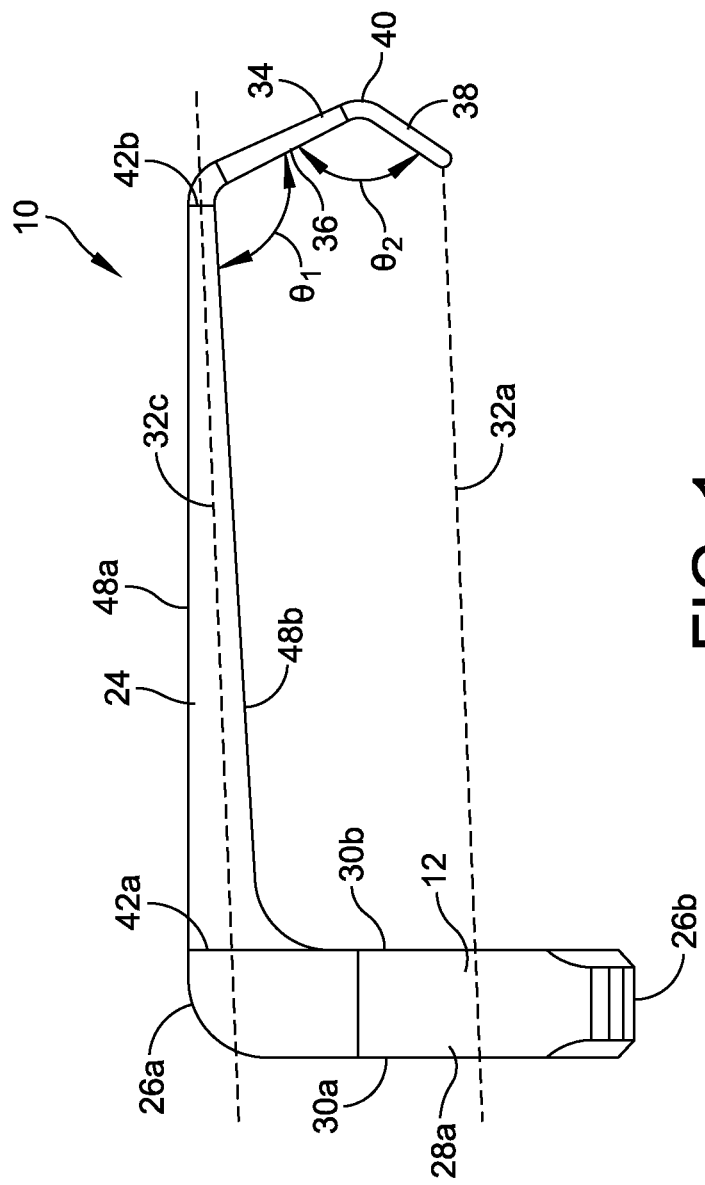
FIG. 1 illustrates a side view of a targeting guide, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a targeting guide is disclosed. The targeting guide includes a body defining one or more guide holes configured to receive a guide sleeve therethrough. A first guide hole extends through the body on a first axis. An alignment arm is coupled to the body at a first end. The alignment arm extends between a first end and a second end. The alignment arm can extend along a horizontal axis, a vertical axis, and/or an arcuate axis. A guide tip extends from the second end of the alignment arm. A portion of the guide tip is aligned with the first axis of the first guide hole such that a guide sleeve and/or a guide element inserted through the guide hole is aligned with the selected portion of the guide tip. A guide element is inserted through the guide sleeve and/or through the guide hole without a guide sleeve and exits the guide sleeve at a position indicated by the predetermined portion of the guide tip.

Figure 2:
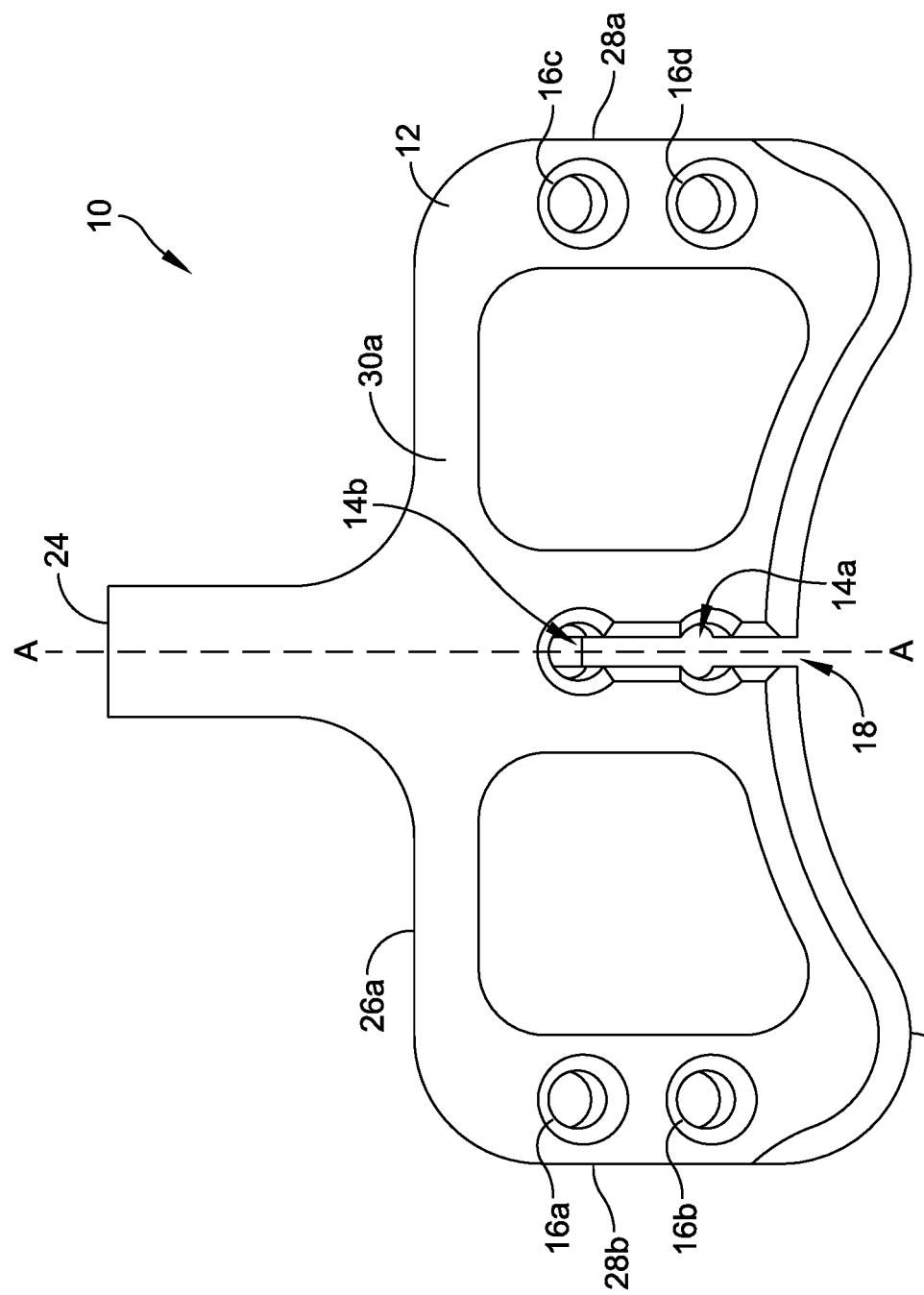
FIG. 2 illustrates a rear view of the targeting guide of FIG. 1, in accordance with some embodiments.
Figure 3:
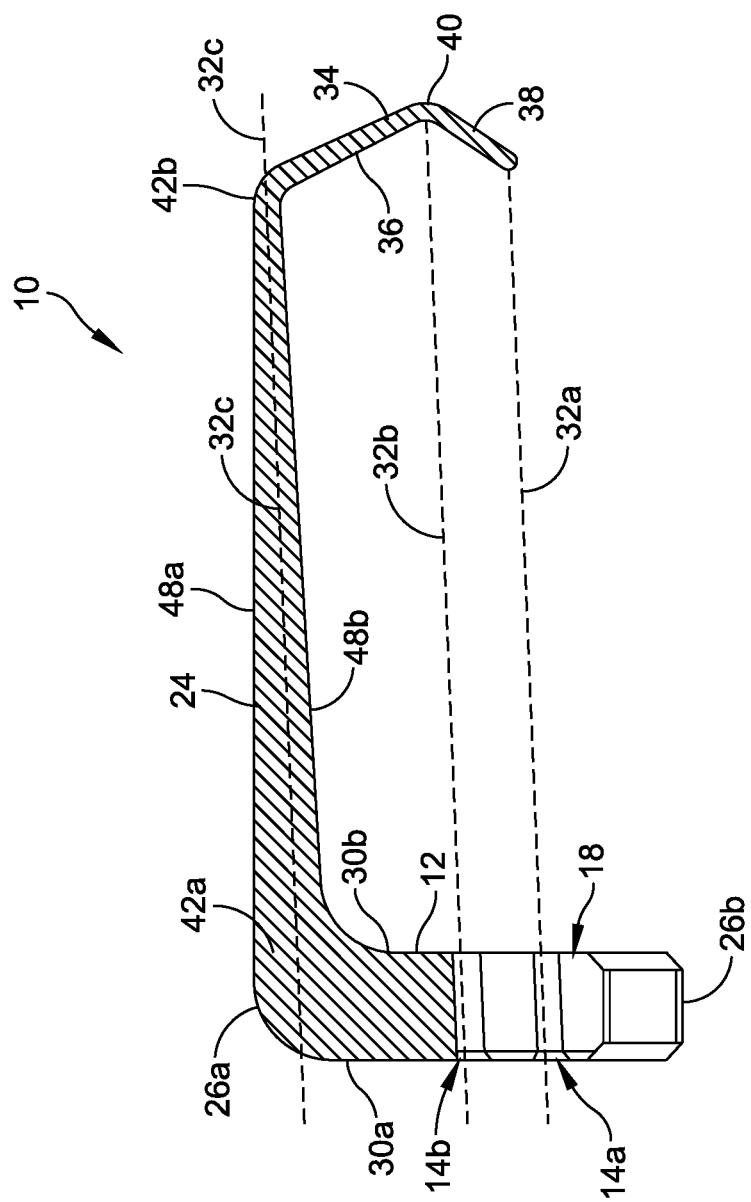
FIG. 3 illustrates a cross-sectional view of the targeting guide taken along line A-A of FIG. 2, in accordance with some embodiments.

FIGS. 1-3 illustrate a targeting guide 10, in accordance with some embodiments. The targeting guide 10 is configured to position one or more guide elements in a bone, as discussed in greater detail with respect to FIGS. 4-10. As best shown in FIGS. 2 and 3, the targeting guide 10 includes a body 12 extending between an upper edge 26a and a lower edge 26b and between a first side 28a and a second side 28b. The body 12 defines a first guide hole 14a and a second guide hole 14b extending through the body 12 from a first surface 30a to a second surface 30b. The first guide hole 14a extends through the body 12 along a first axis 32a and the second guide hole 14b extends through the body 12 along a second axis 32b. In some embodiments, the first axis 32a and the second axis 32b are substantially parallel, although it will be appreciated that the first and second axes 32a, 32b can define non-parallel (e.g., intersecting) paths. Each of the guide holes 14a, 14b are sized and configured to receive a guide sleeve therethrough (see FIG. 4).

In some embodiments, a channel 18 extends from a lower edge 26b of the body 12 into an interior portion of the body 12. The channel 18 is sized and configured to receive one or more guide elements therethrough such that the targeting guide 10 can be removed from a surgical site after insertion of one or more guide elements, as discussed in greater detail below with respect to FIGS. 4-10. Although embodiments are illustrated including a channel 18 extending from a bottom edge 26b of the body 12, it will be appreciated that the channel 18 can extend inward from any outer surface of the body 12 and/or can be omitted in various embodiments.

In some embodiments, an alignment arm 24 extends from an upper edge 26a of the body 12. The alignment arm 24 extends from a first end 42a (coupled to the body 12) to a second end 42b. In some embodiments, a guide tip 34 is coupled to the second end 42b of the alignment arm 24. The alignment arm 24 has a predetermined length configured to position the guide tip 34 at a predetermined distance from the body 12. In some embodiments, the predetermined distance corresponds to an anatomical feature of a patient. In the illustrated embodiment, the alignment arm 24 extends on a horizontal axis 32c, although it will be appreciated that the alignment arm 24 can include any number of segments extending along one or more horizontal, vertical, and/or arcuate axes, such as one straight segment, a plurality of short straight segments, an arc of some curvature, etc. Although embodiments are discussed herein including an alignment arm 24 having a predetermined length, it will be appreciated that the alignment arm 24 can have a telescoping or non-fixed length in some embodiments.

In some embodiments, the alignment arm 24 is tapered from the first end 42a to the second end 42b. The bottom edge 48b of the alignment arm 24 can be tapered such that the thickness of the alignment arm 24 decreases from the first end 42a to the second end 42b while maintaining a horizontal axis 32c aligned with the first axis 32a and the second axis 32b of respective first and second guide holes 14a, 14b. In other embodiments, the upper edge 48a can be tapered in addition to and/or alternatively to the bottom edge 48b. In some embodiments, the alignment arm 24 is tapered from a first thickness, corresponding to a thickness of the body 12, to a second thickness, corresponding to a thickness of a guide tip 34.

The guide tip 34 extends from the second end 42b of the alignment arm 24. The guide tip 34 is configured to indicate a position related to one or more guide elements inserted through the targeting guide 10. For example, in some embodiments, a portion of the guide tip 34 corresponds to an exit position from a first bone portion of one or more guide elements inserted through the guide holes 14a, 14b of the targeting guide 10. The guide tip 34 can include an intermediate portion 36, a terminal portion 38, a free end 38a, and a transition 40 between the intermediate portion 36 and the terminal portion 38, each of which may correspond to a position of one or more guide elements.

In the illustrated embodiment, the guide tip 34 includes an intermediate portion 36 extending from the alignment arm 24 and a terminal portion 38 extending from the intermediate portion 36. The guide tip 34 extends a predetermined distance from the alignment arm 24 such that a free end 38a of the terminal portion 38 is aligned with the first axis 32a of the first guide hole 14a. The terminal portion 38 is configured to be positioned against a surface of a bone to indicate an exit position of a first guide element inserted into the bone through the targeting guide 10 such that a user (such as a surgeon) can visualize the position of the first guide element prior to inserting the guide element into the bone, reducing the number of reinsertions required during surgery.

In some embodiments, the intermediate portion 36 extends a predetermined length such that the terminal portion 38 is positioned at a predetermined distance from the interface between the alignment arm 24 and the guide tip 34. The intermediate portion 36 extends from the alignment arm 24 at a first angle $\Theta 1$ and the terminal portion 38 extends from the intermediate portion 36 at a second angle $\Theta 2$. In some embodiments, a junction 40 between the intermediate portion 36 and the terminal portion 38 corresponds to an exit position of a guide element inserted through one of the guide holes 14a, 14b defined by the body 12. Although embodiments are discussed herein including an intermediate portion 36, it will be appreciated that the intermediate portion 36 can be omitted and the terminal portion 38 can extend directly from the alignment arm 24, in some embodiments. In other embodiments, additional intermediate portions can be disposed between the alignment arm 24 and the terminal portion 38 each corresponding to additional and/or alternative guide holes or guide hole axes. In other embodiments, the intermediate portion 36 and/or the terminal portion 38 extend from the alignment arm 24 in a continuous and/or variable arc.

FIGS. 4-10 illustrate the targeting guide 10 in use at a surgical site 100. The surgical site 100 includes a plurality of bones, such as a first bone 102 and a second bone 104. In the illustrated embodiment, the first bone 102 is a metatarsal and the second bone 104 is a proximal phalanx, although it will be appreciated that the first bone 102 and/or the second bone 104 can be any suitable bones, such as one or more hand bones, foot bones, etc. The targeting guide 10 discussed above in conjunction with FIGS. 1-3, and similar description is not repeated herein.

In use, the lower surface 26b of the body 12 of the targeting guide 10 is positioned against an outer surface of a patient adjacent to a first bone 102, such as an outer surface of a foot adjacent to a metatarsal. The guide tip 34 is positioned against a distal end of a first portion 102a of the bone 102. In some embodiments, the first portion 102a includes a bone fragment formed during a medical procedure (such as an osteotomy), formed during an injury, and/or otherwise separated from a second portion 102b. A first guide sleeve 116a is inserted through the first guide hole 14a in the body 12 and a second guide sleeve 116b is inserted through the second guide hole 14b in the body 12. The first guide sleeve 116a extends along the first axis 32a when inserted through the first guide hole 14a and the second guide sleeve 116b extends along the second axis 32b when inserted through the second guide hole 14b. The first and second guide sleeves 116a, 116b are positioned in contact with and/or adjacent to the first bone fragment 102a.

Figure 4:
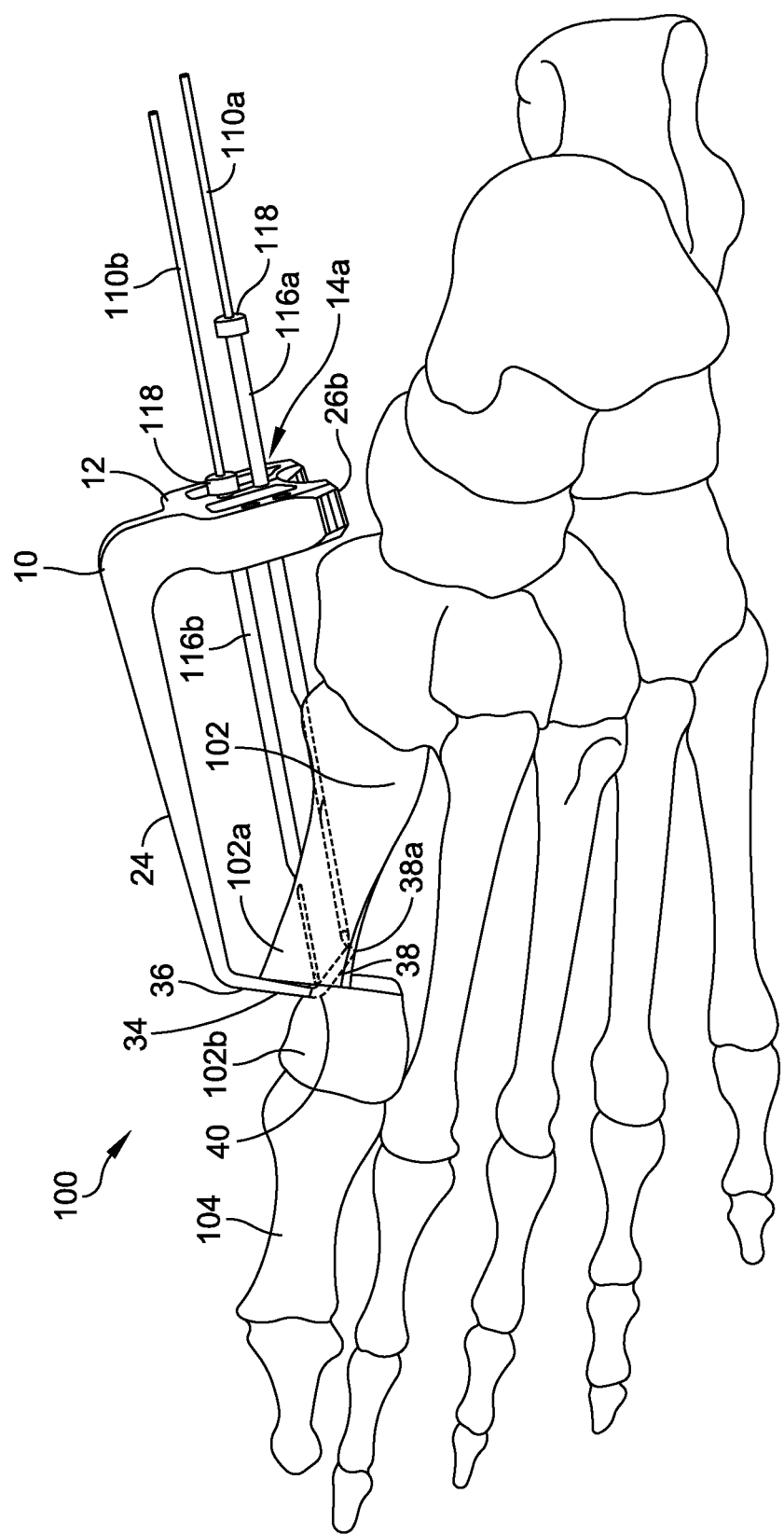
FIG. 4 illustrates a surgical site having a targeting guide positioned adjacent to a first bone portion, in accordance with some embodiments.

In some embodiments, each of the guide sleeves 116a, 116b define a central channel sized and configured to receive a guide element therethrough. The central channels are concentric with respective axes 32a, 32b such that a guide element inserted through the guide sleeves 116a, 116b extends along the respective axis 32a, 32b. For example, as shown in FIG. 4, a first guide element 110a is inserted through the first guide sleeve 116a along the first axis 32a and a second guide element 110b is inserted through the second guide sleeve 116b along the second axis 32b. In some embodiments, each of the guide sleeves 116a, 116b include a flared or larger-diameter portion 118 configured to prevent insertion of the guide sleeve 116a, 116b through the guide holes 14a, 14b, although it will be appreciated that the flared portion 118 can be omitted. The first and second guide elements 110a, 110b can include any suitable guide elements configured to guide a fastener to an implantation site and/or form a pilot hole. For example, in the illustrated embodiment, each of the first and second guide elements 110a, 110b include a k-wire, although it will be appreciated that any suitable guide element, such as a pin, a wire, a screw, etc., can be used.

Figure 5:
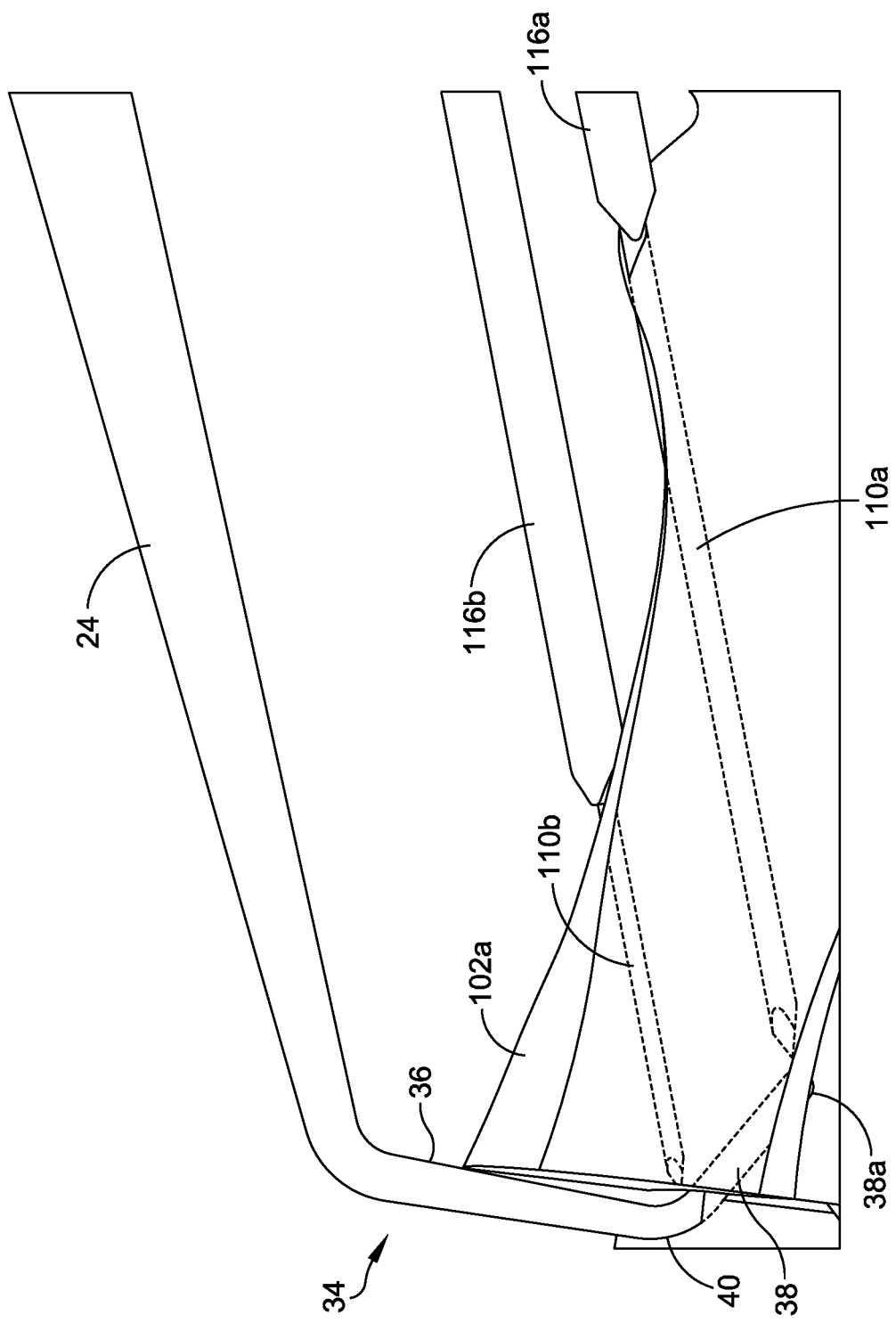
FIG. 5 illustrates the surgical site of FIG. 4 having a first guide sleeve and a second guide sleeve positioned through respective first and second guide holes of the targeting guide, in accordance with some embodiments.

As best shown in FIG. 5, the alignment arm 24 and guide tip 34 of the targeting guide 10 are configured to provide visualization of a position of the guide elements 110a, 110b prior to insertion. A free end 38a of the terminal portion 38 is aligned with the first axis 32a of the first guide hole 14a. When the targeting guide 10 is positioned adjacent to and/or in contact with the first bone portion 102a, the free end 38a is positioned at an exit point of the first guide element 110a when inserted through the first guide sleeve 116a and the first bone fragment 102a. In some embodiments, the junction 40 between the intermediate portion 36 and the terminal portion 38 of the guide tip 34 corresponds to a position of a second guide element 110b when inserted through the second guide sleeve 116b and the first bone fragment 102a. The terminal portion 36 can be used to position and align the targeting guide 10 prior to insertion of the first or second guide elements 110a, 110b, ensuring the guide elements 110a, 110b are properly placed and eliminated the need for repeated removal and reinsertion of the guide elements 110a, 110b. In some embodiments, the guide elements 110a, 110b can be inserted until they abut a predetermined portion of the guide tip 34, such as the terminal portion 38, the junction 40, and/or any other suitable portion. In other embodiments, the guide elements 110a, 110b can be inserted partially into the first bone 102 without contacting the guide tip 34. In some embodiments, the guide tip 34 defines one or more holes sized and configured to receive guide elements 110a, 110b therethrough.

In some embodiments, the body 12 includes one or more alignment holes 16a-16d. The alignment holes 16a-16d are configured to receive a guide element therethrough, such as a k-wire. The alignment holes 16a-16d have axes aligned with the axes 32a, 32b of the guide holes 14a, 14b. A guide element positioned through one of the alignment holes 16a-16d is positioned parallel with a guide sleeve 116a, 116b and/or a guide element 110a, 110b inserted through a respective guide hole 14a, 14b and provides a visual indicator of the position of the guide sleeves 116a, 116b and/or guide elements 110a, 110b with respect to an anatomical structure, such as a first bone. For example, in some embodiments, the alignment holes 16a-16d allow a user (e.g., a surgeon) to position one or more guide elements externally of a patient's anatomy to visually align the targeting guide 10 with the anatomical structure. In some embodiments, the alignment holes 16a-16d are omitted.

Figure 6:
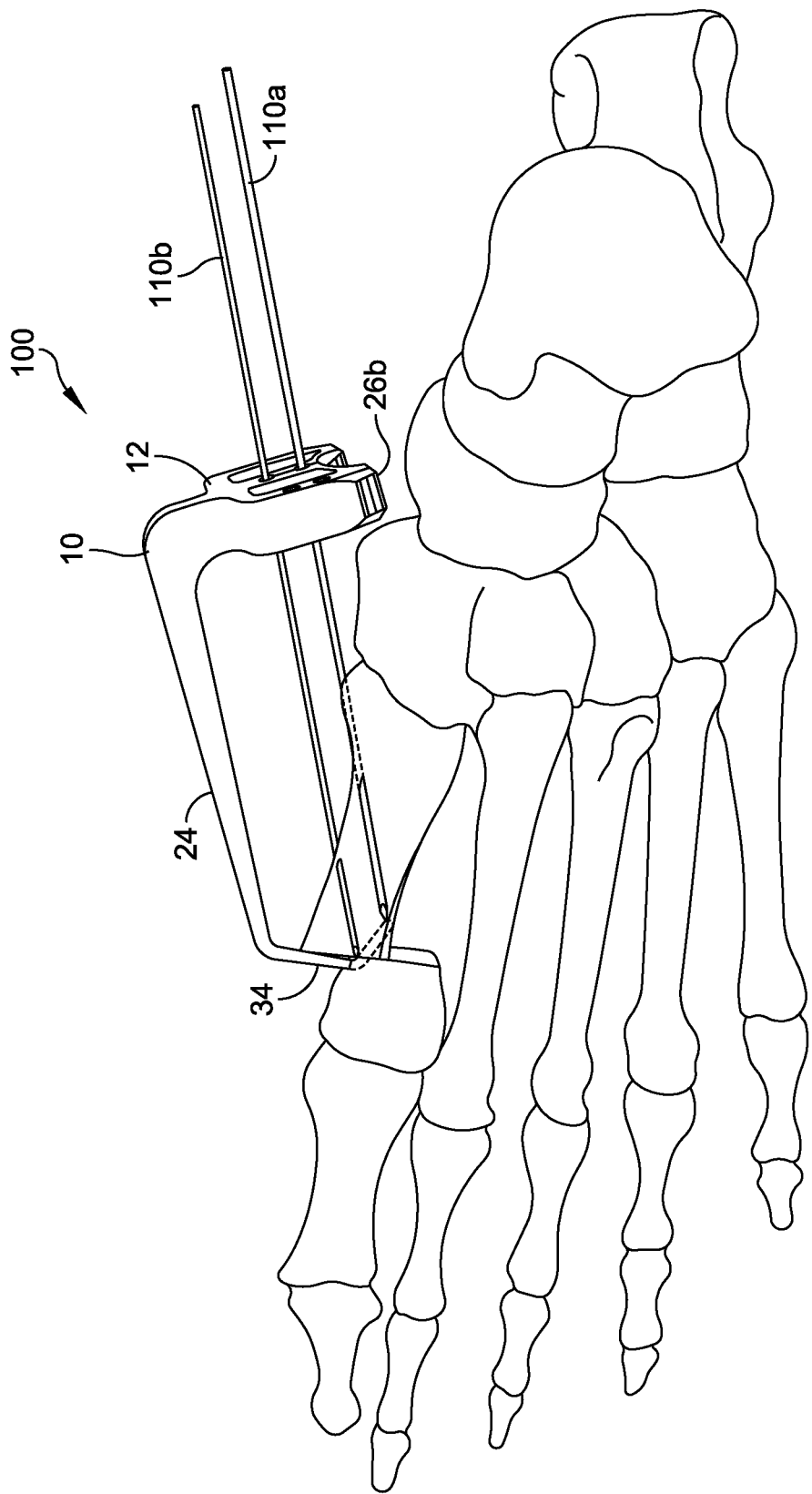
FIG. 6 illustrates the surgical site of FIG. 5 having the first guide sleeve and the second guide sleeve removed therefrom, in accordance with some embodiments.
Figure 7:
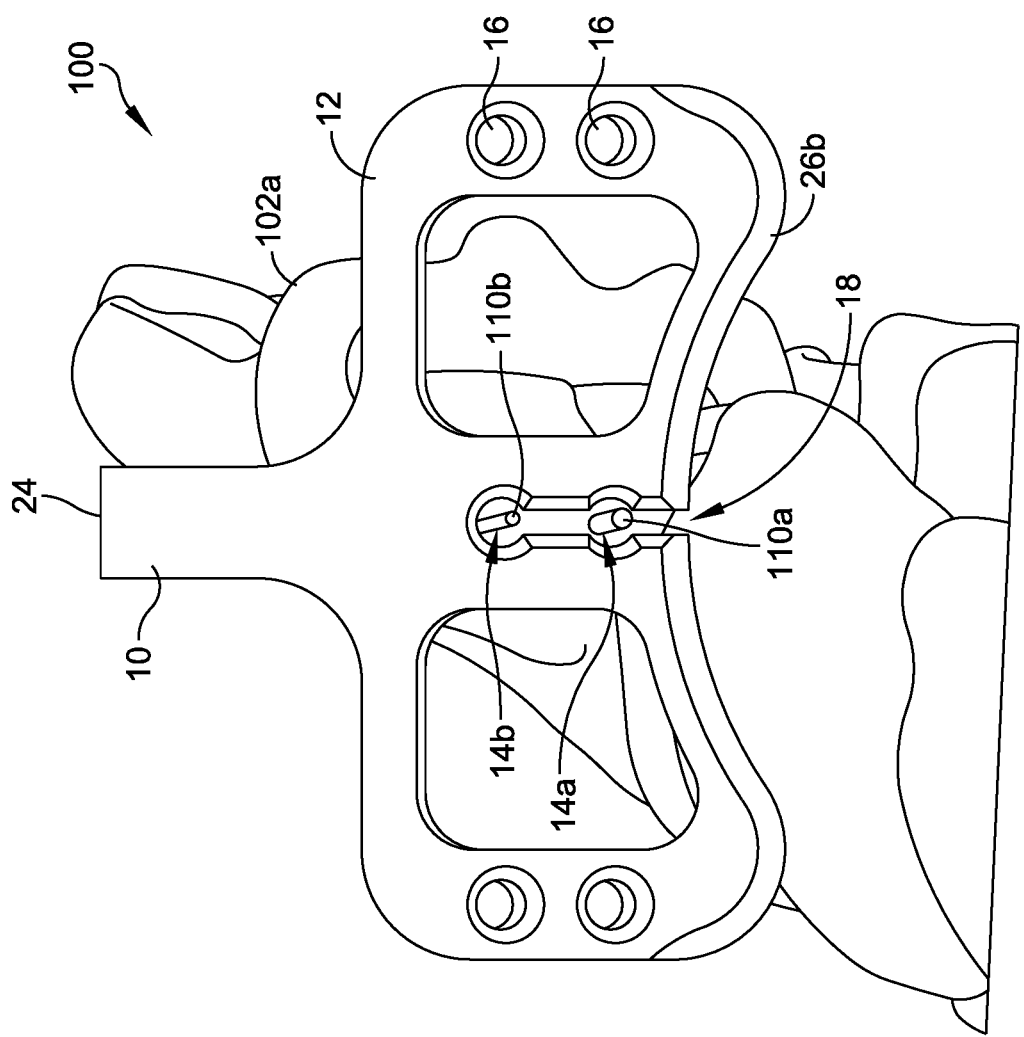
FIG. 7 illustrates a rear view of the surgical site of FIG. 6, in accordance with some embodiments.

As best shown in FIG. 6, the guide sleeves 116a, 116b can be removed from the targeting guide 10 and/or the guide elements 110a, 110b after insertion of the guide elements 110a, 110b. In some embodiments, the guide sleeves 116a, 116b are slideably removed proximally over the guide elements 110a, 110b, although it will be appreciated that the guide element 110a, 110b can be removed in any suitable direction. The targeting guide 10 is used to visually verify placement of the first guide element 110a and the second guide element 110b in the first bone fragment 102a. For example, as shown in FIG. 7, in some embodiments, positioning of the guide elements 110a, 110b is checked by verifying that the guide elements are centered within the guide holes 14a, 14b, and/or verify contact between a predetermined portion of the guide tip 34 and the guide elements 110a, 110b, although it will be appreciated that other visual indications can be used to verify placement of the guide elements 110a, 110b. Any suitable visualization technique, such x-ray imaging, fluoroscopy, etc. can be used to image and verify the targeting guide prior to and/or after insertion of the guide elements 110a, 110b.

Figure 8:
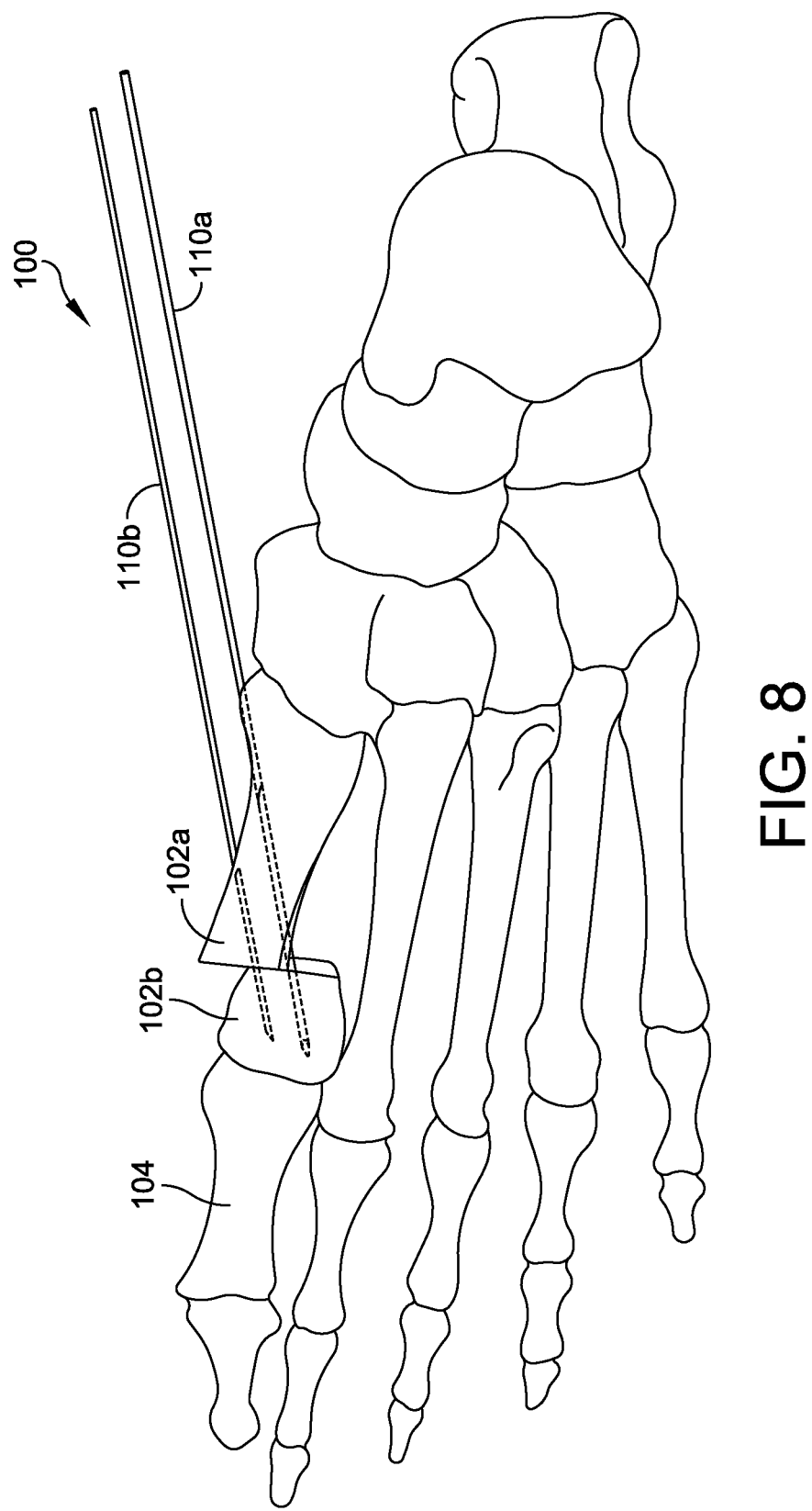
FIG. 8 illustrates the surgical site of FIG. 6 having the targeting guide removed therefrom, in accordance with some embodiments.

As best shown in FIG. 8, the targeting guide 10 can be removed from the surgical site 100. For example, the targeting guide 10 can be removed by advancing the targeting guide 10 in a direction away from the first bone 102. The channel 18 allows the targeting guide 10 to be removed from the surgical site 100 without interfering with the guide elements 110a, 110b, as the guide elements 110a, 110b traverse the channel 18 when the targeting guide 10 is removed. Prior to and/or after removal of the targeting guide 10, the guide elements 110a, 110b can be advanced into the second bone fragment 102b.

Figure 9A:
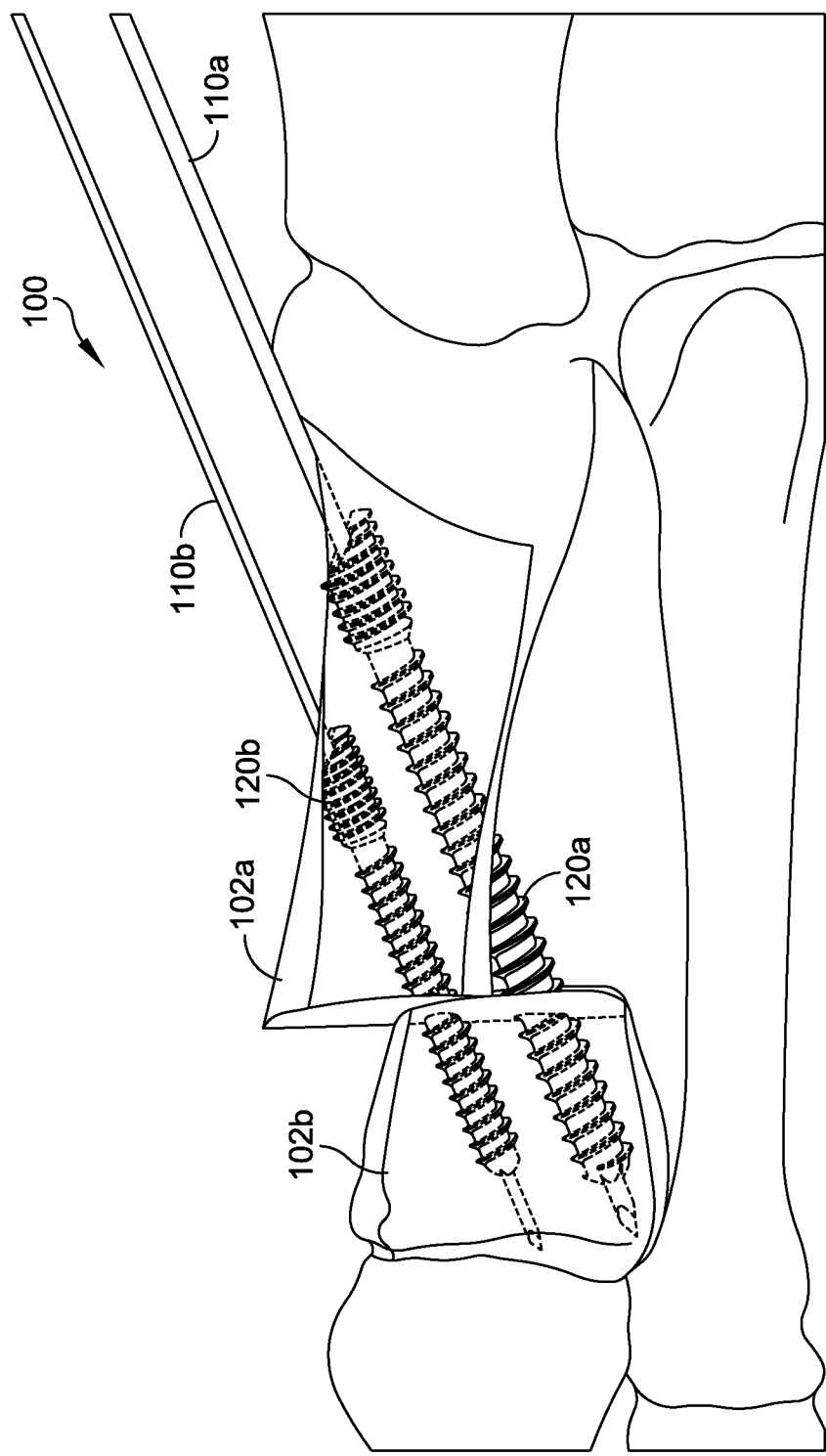
FIG. 9A illustrates the surgical site of FIG. 8 having a first fixation device and a second fixation device inserted into the first bone portion and a second bone portion, in accordance with some embodiments.
Figure 9B:
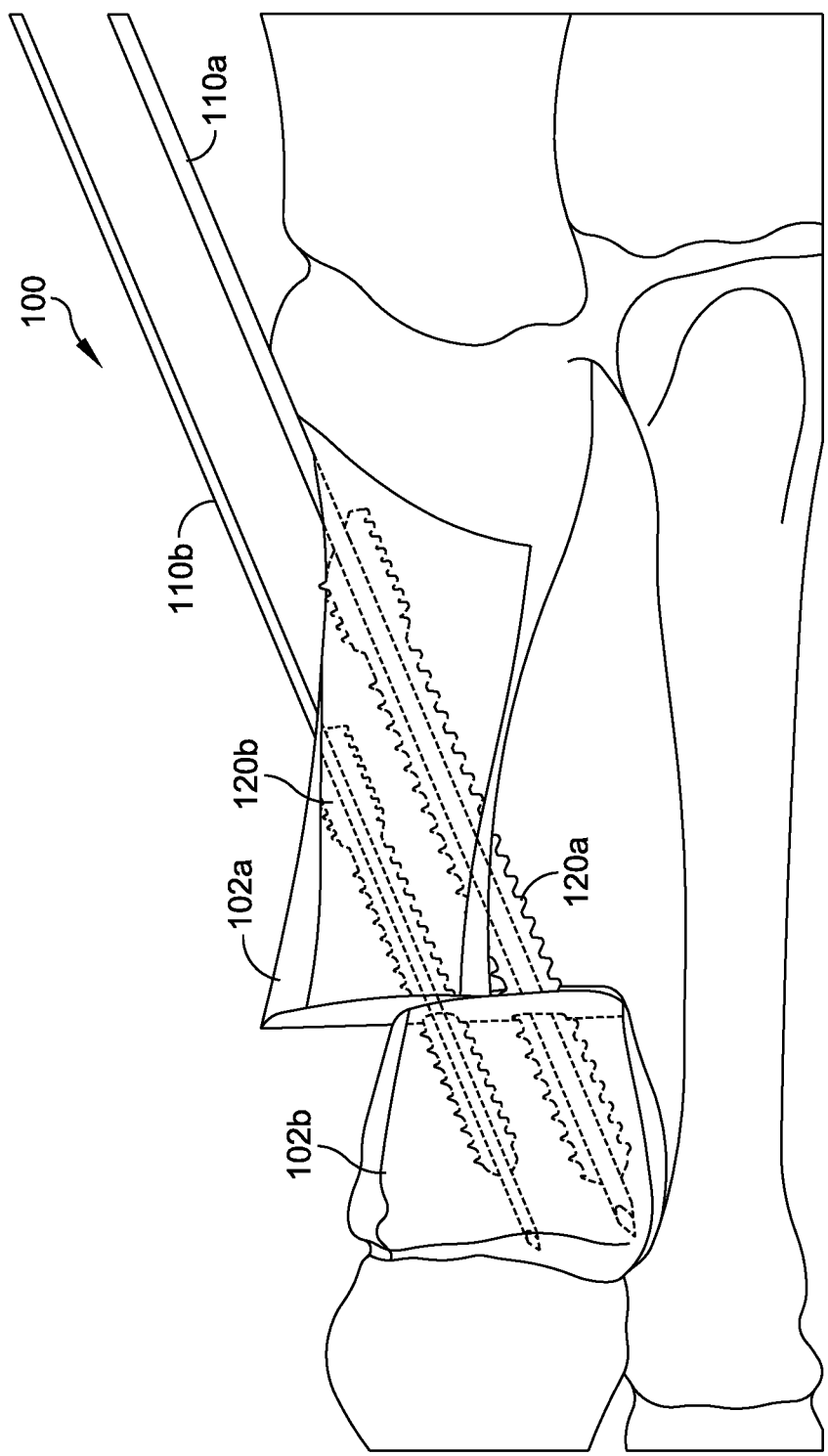
FIG. 9B illustrates a cross-sectional view of the fixation devices of FIG. 9A, in accordance with some embodiments.

The guide elements 110a, 110b can be inserted into the second bone fragment 102b to temporarily fix the position of the first bone fragment 102a and the second bone fragment 102b. In some embodiments, a fixation element can be inserted over the guide elements 110a, 110b. For example, as shown in FIG. 9A, in some embodiments, a first cannulated screw 120a is slideably positioned over the first guide element 110a and inserted through the first bone fragment 102a and the second bone fragment 102b and a second cannulated screw 120b is slideably positioned over the second guide element 110b and inserted through the first bone fragment 102a and the second bone fragment 102b. The first and second cannulated screws 120a, 120b fix the relative positions of the first bone fragment 102a and the second bone fragment 102b. The guide elements 110a, 110b can be removed from the bone 102 after fixation of the bone by the fixation elements 120a, 120b. FIG. 9B illustrates a cross-sectional view of the screws 120a, 120b having guide elements 110a, 110b extending therethrough.

Although embodiments are illustrated including cannulated screws 120a, 120b, it will be appreciated that any suitable fixation device can be coupled to the first bone fragment 102a and/or the second bone fragment 102b. For example, in some embodiments, cannulated fasteners (such as a cannulated screw, peg, pin, etc.) are inserted over each of the guide elements 110a, 110b to fix the position of the first bone fragment 102a and the second bone fragment 102b. As another example, in some embodiments, the guide elements 110a, 110b can be removed from the first and second bone fragments 102a, 102b and fasteners, such as cannulated and/or non-cannulated fasteners, can be inserted into the guide holes formed by the guide elements 110a, 110b in the first and second bone fragments 102a, 102b. It will be appreciated that additional and/or alternative fasteners and insertion methods can be used.

In various embodiments, the targeting guide 10 can include one or more alignment features configured to assist in and/or provide verification of the alignment of the targeting guide 10 prior to and/or during insertion of the guide elements 110a, 110b. For example, in some embodiments, the targeting guide 10 can include one or more alignment holes 16a-16d formed through the body 12, one or more alignments holes formed through the alignment arm 24 (as discussed below with respect to FIGS. 10-12), one or more alignment protrusions (as discussed below with respect to FIGS. 13-14), a fluoroscopic and/or other imaging compatible alignment element, laser markings, and/or any other suitable alignment feature.

Figure 10:
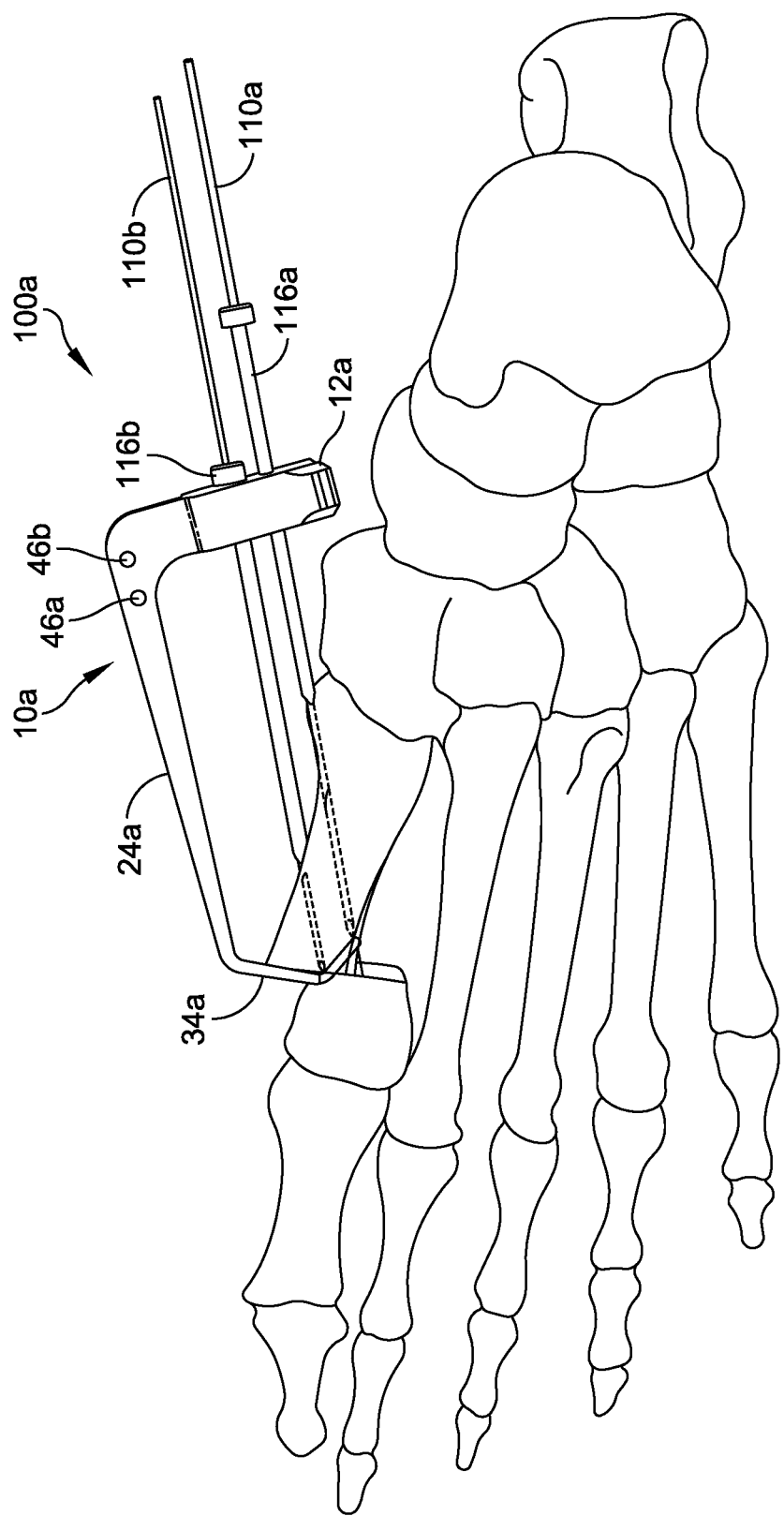
FIG. 10 illustrates a surgical site including a targeting guide having a first alignment hole and a second alignment hole, in accordance with some embodiments.
Figure 11:
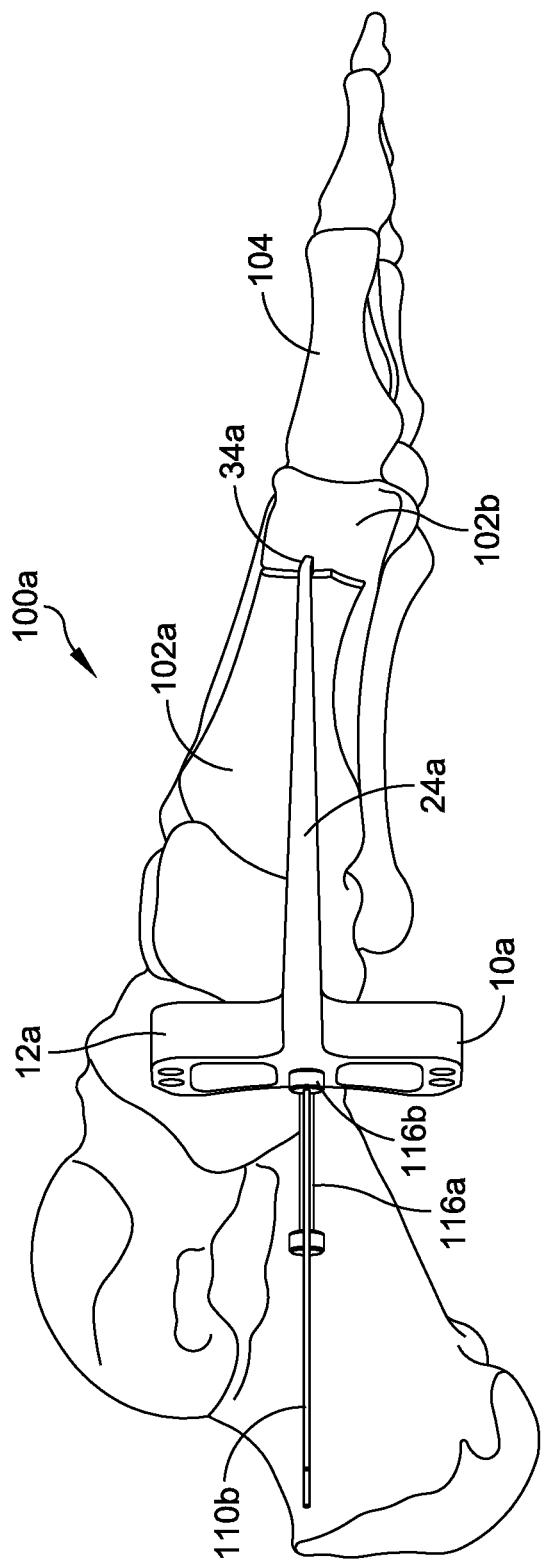
FIG. 11 illustrates a side view of the surgical site of FIG. 10, in accordance with some embodiments.
Figure 12:
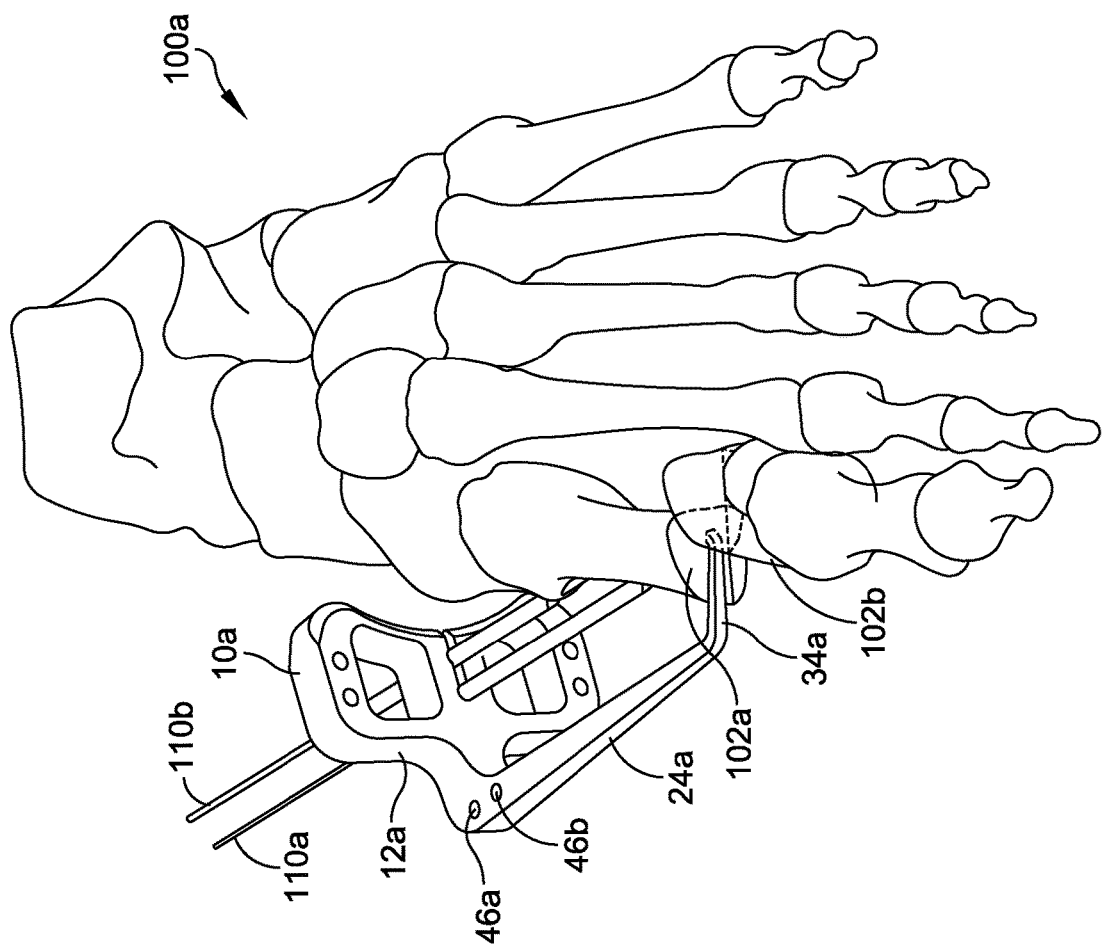
FIG. 12 illustrates a front view of the surgical site of FIG. 10, in accordance with some embodiments.

FIGS. 10-12 illustrate a surgical site 100a including a targeting guide 10a having a plurality of lateral alignment holes 46a, 46b formed through the alignment arm 24a, in accordance with some embodiments. The surgical site 100a and the targeting guide 10a are similar to the surgical site 100 and the targeting guide 10 discussed above in conjunction with FIGS. 1-9, and similar description is not repeated herein. The alignment guide 10a includes a first lateral alignment hole 46a and a second lateral alignment hole 46b extending through the alignment arm 24a. The first and second lateral alignment holes 46a, 46b are configured to provide a visual indication to a user (such as a surgeon) regarding an alignment of the targeting guide 10a when the guide tip 24a is positioned adjacent to the first bone portion 102a.

In some embodiments, the lateral alignment holes 46a, 46b are positioned such that no portion of the hole 46a, 46b is visible from a predetermined angle when the targeting guide 10a is viewed from a predetermined angle. For example, as shown in FIG. 11, when the targeting guide 10a is aligned with the first bone portion 102a and is viewed from a side angle, the first and second lateral alignment holes 46a, 46b are not visible. In this configuration, the alignment arm 24a of the targeting guide 10a will be aligned with an axis of the first bone portion such that the guide tip 34a indicates an exit location of one or more guide elements 110a, 110b as discussed above.

Figure 13:
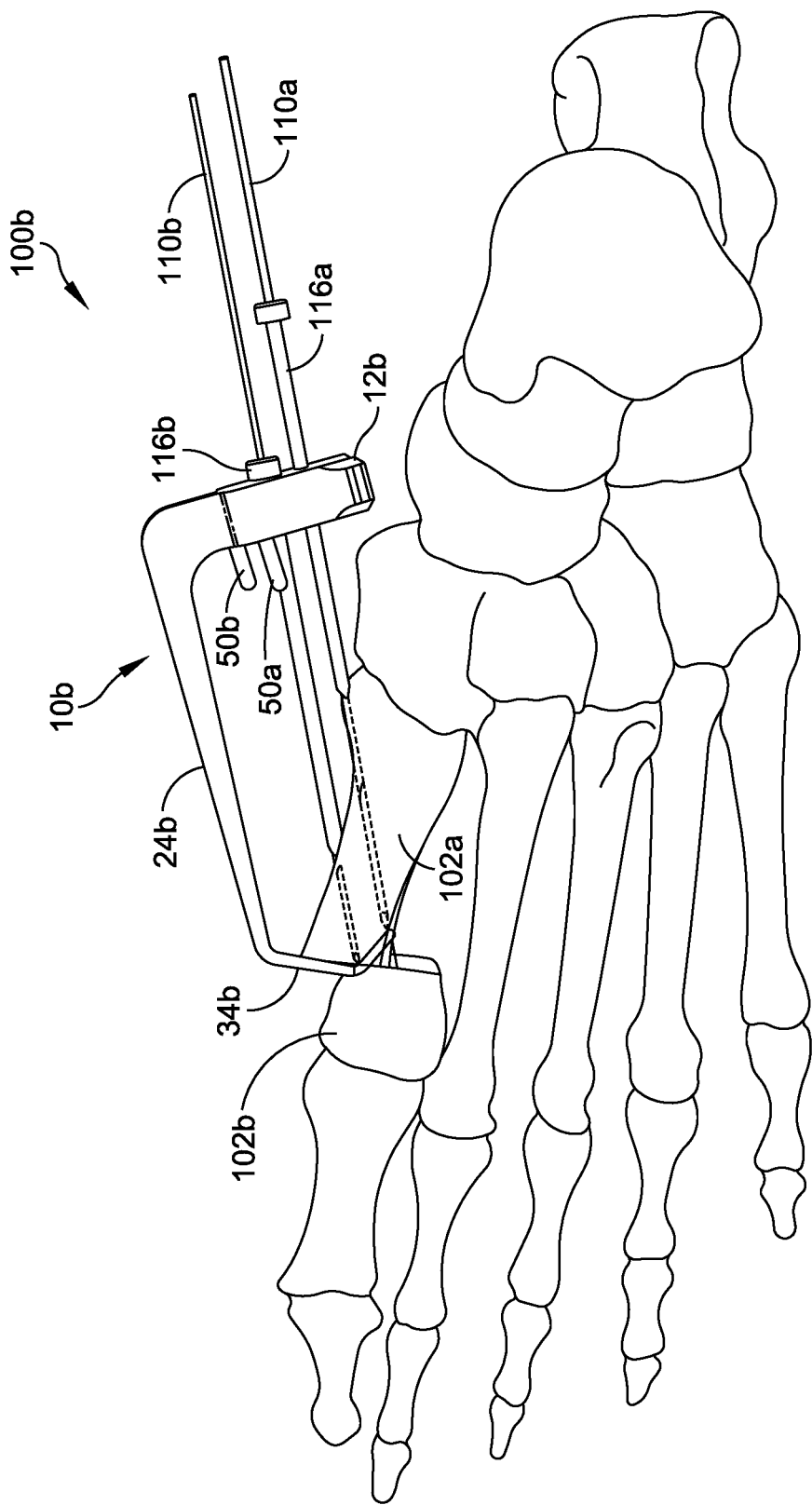
FIG. 13 illustrates a surgical site including a targeting guide having a first alignment pin and a second alignment pin, in accordance with some embodiments.
Figure 14:
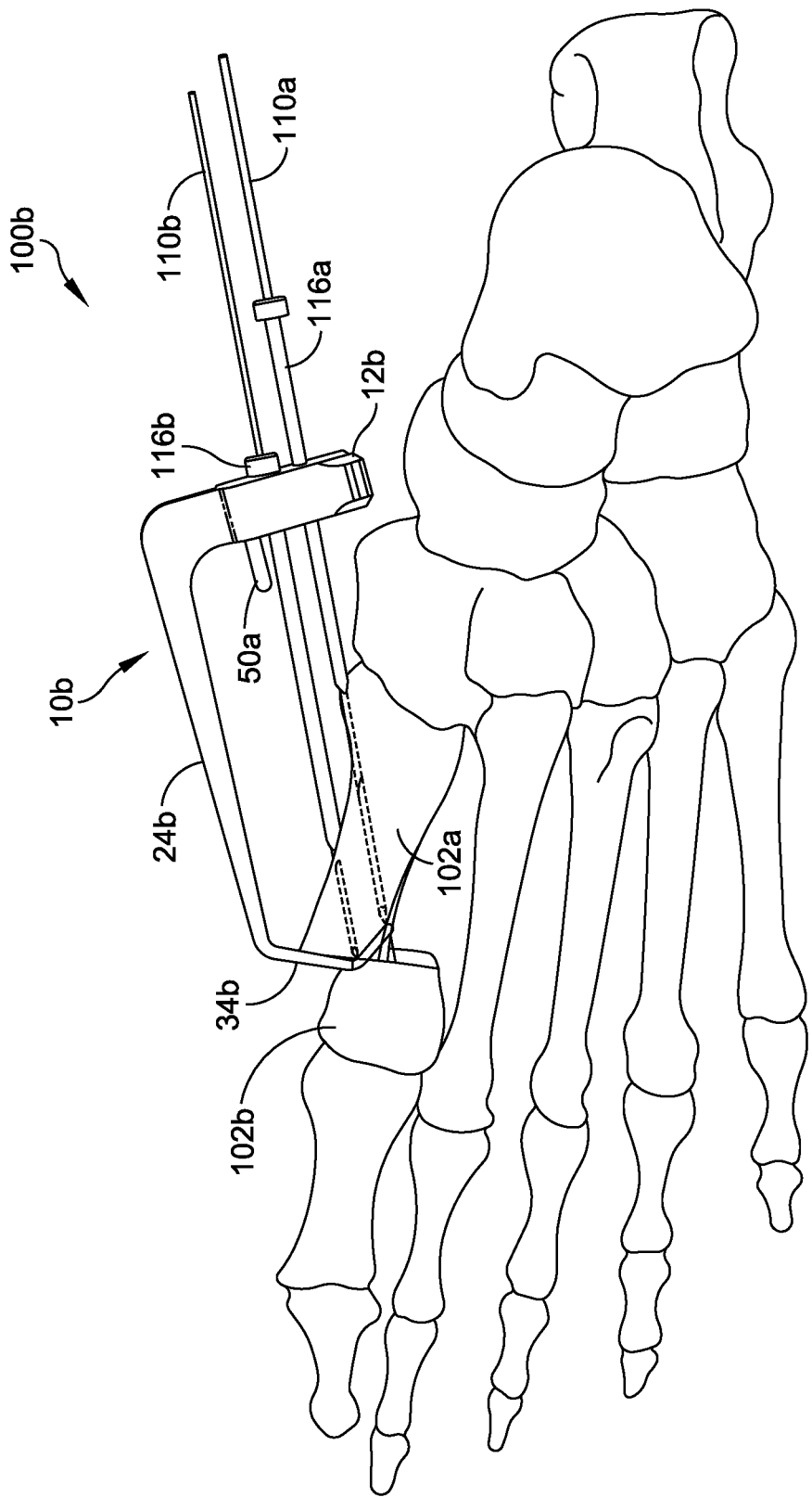
FIG. 14 illustrates the targeting guide of FIG. 13 having the first alignment pin and the second alignment pin aligned on a predetermined axis, in accordance with some embodiments.

FIGS. 13-14 illustrate a surgical site 100b including a targeting guide 10b having a first alignment protrusion 50a and a second alignment protrusion 50b. The alignment protrusions 50a, 50b extend from second surface 30b of the body 12b, although it will be appreciated that alignment protrusions 50a, 50b can extend from any suitable portion of the targeting guide 10b, such as the body 12b, the alignment arm 24b, and/or the guide tip 34b. The alignment pins 50a, 50b are aligned on an alignment axis such that when the targeting guide 10b is rotationally aligned with the first bone 102, the first and second alignment pins 50a, 50b are vertically aligned.

For example, as shown in FIG. 13, when the targeting guide 10b is not properly aligned with the first bone 102, the alignment protrusions 50a, 50b are not vertically aligned and are each visible from a top view of the surgical site 100b. As shown in FIG. 14, when the targeting guide 10b is properly aligned with the first bone 102a, the alignment protrusions 50a, 50b are vertically aligned and only one of the alignment protrusions 50a is visible, as the second alignment protrusion 50b is hidden behind the first alignment protrusion 50a. In some embodiments, additional alignment protrusions can be included to provide different alignment axes and/or different alignment viewing angles.

FIGS. 15-21 illustrate additional embodiments of a targeting guide, in accordance with various embodiments. Although certain features may be illustrated in some embodiments but not others, it will be appreciated that features of anyone embodiment can be combined with features and/or elements of any other disclosure. For example, the targeting guide 10 includes a slot 18 extending from a bottom edge. Each of the targeting guides illustrated in FIGS. 15-21 can include a slot extending inward from any portion of the body. Other potential combinations and/or modifications will be apparent and is within the scope of this disclosure.

Figure 15:
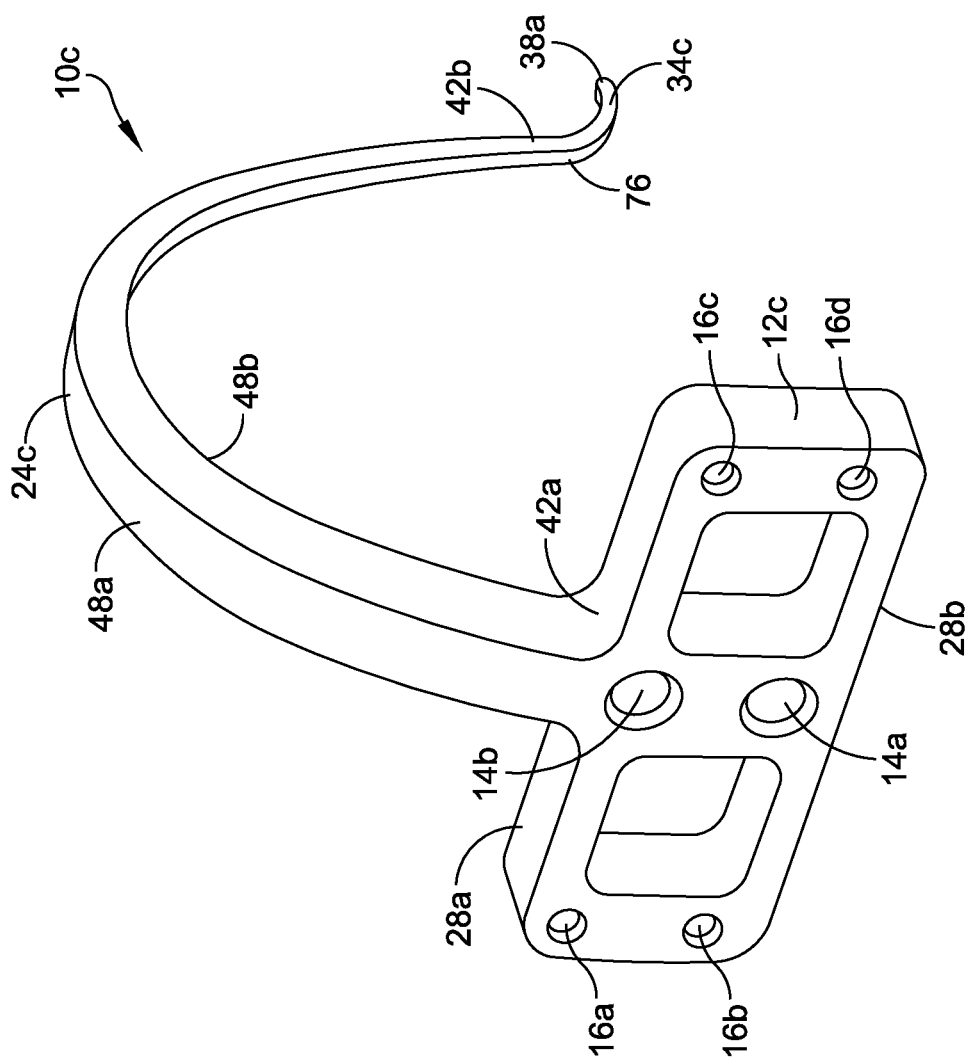
FIG. 15 illustrates a targeting guide having an arced alignment arm extending from a body, in accordance with some embodiments.

FIG. 15 illustrates a targeting guide 10c having an arced alignment arm 24c extending from a body 12c, in accordance with some embodiments. The targeting guide 10c is similar to the targeting guide 10 discussed above in conjunction with FIGS. 1-9, and similar description is not repeated herein. The alignment arm 24c of the targeting guide 10c extends from a first end 42a coupled to the body 12c to a second end 42b along an arcuate axis. The arc of the alignment arm 24 is selected such that a predetermined portion of the guide tip 34c coupled to the alignment arm 24c is aligned with an axis of at least one guide hole 14a, 14b extending through the body 12c, as discussed in greater detail below.

In some embodiments, the alignment arm 24c is tapered from the first end 42a to the second end 42b. For example, in some embodiments, the upper edge 48a of the alignment arm 24c extends along a first arc and the bottom edge 48b of the alignment arm 24c extends along a second arc such that the thickness of the alignment arm 24c decreases from the first end 42a to the second end 42b. In other embodiments, the upper edge 48a and/or the bottom edge 48b can have a variable arc.

The body 12c of the targeting guide 10c can include a rectangular shape having a flat bottom edge 28b. The bottom edge 28b is configured to abut and/or rest against an outer surface of a patient, such as an outer surface of a foot. Although embodiments are illustrated with a rectangular body 12c, it will be appreciated that the body 12c can have any suitable shape. The body 12c can be curved from a first side 28a to a second side 28 and/or can be flat.

In some embodiments, the guide tip 34c extends from the alignment arm 24c along a predetermined arc. For example, in the illustrated embodiment, the guide tip 34c extends in a direction generally opposite of the arcuate direction of the alignment arm 24c. The guide tip 34c can have a transition (or bend) 76 that corresponds to a change between the arc of the alignment arm 24c and the arc of the guide tip 34c. In some embodiments, the transition 76 can correspond to a horizontal axis of one of the guide holes 14a, 14b formed in the body 12c and the free end 38a of the guide tip 34c corresponds to a horizontal axis of a second of the guide holes 14a, 14b. In the illustrated embodiment, the guide tip 34c extends generally upward from a transition 76 (and away from the body 12c), although it will be appreciated that the guide tip 34c can extend in any suitable direction from the alignment arm 24c such that a portion of the guide tip 34c corresponds to a horizontal axis of one of the guide holes 14a, 14b, as discussed above.

Figure 16:
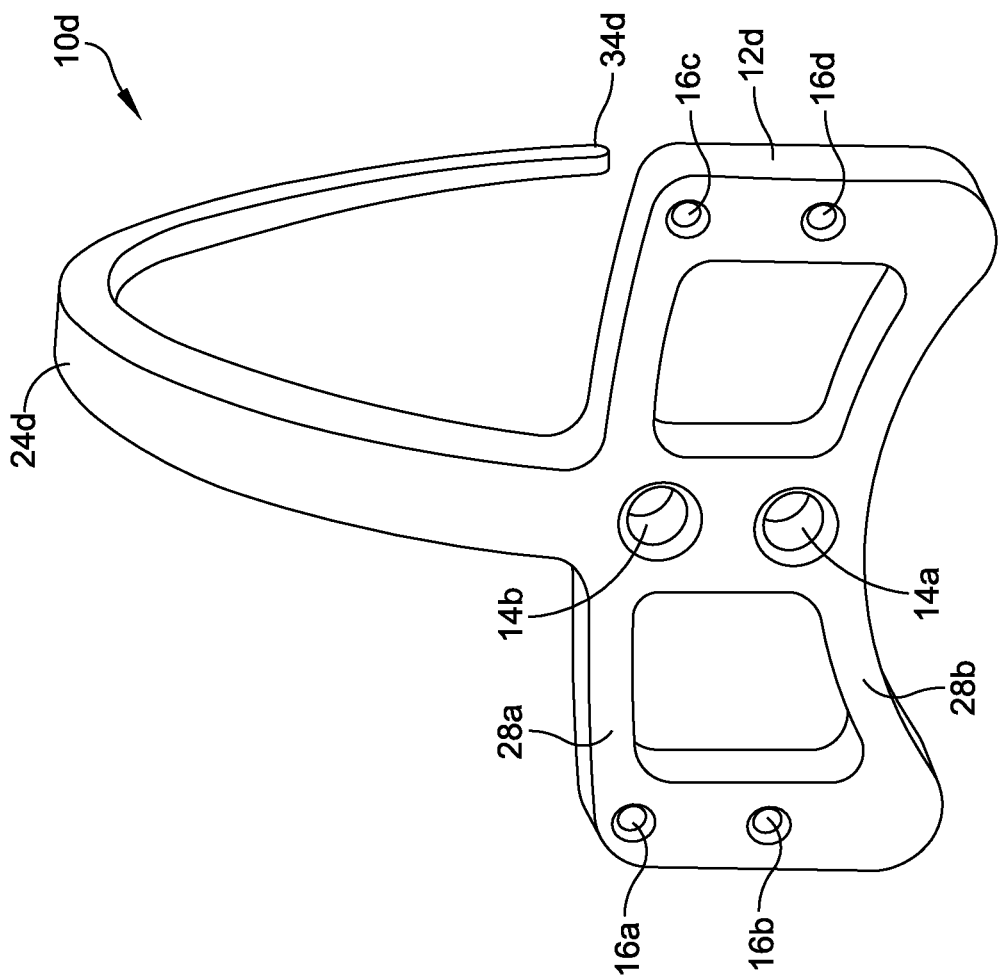
FIG. 16 illustrates a targeting guide having an arced alignment arm and a curved lower surface of a body, in accordance with some embodiments.

FIG. 16 illustrates a targeting guide 10d having an arced alignment arm 24d and a curved lower surface 28b of a body 12d, in accordance with some embodiments. The targeting guide 10d is similar to the targeting guide 10c discussed above in conjunction with FIG. 15, and similar description is not repeated herein. The targeting guide 10d includes a curved lower surface 26b configured to conform to an outer surface of a patient, such as an outer surface of a foot, hand, shoulder, elbow, knee, etc.

Figure 17:
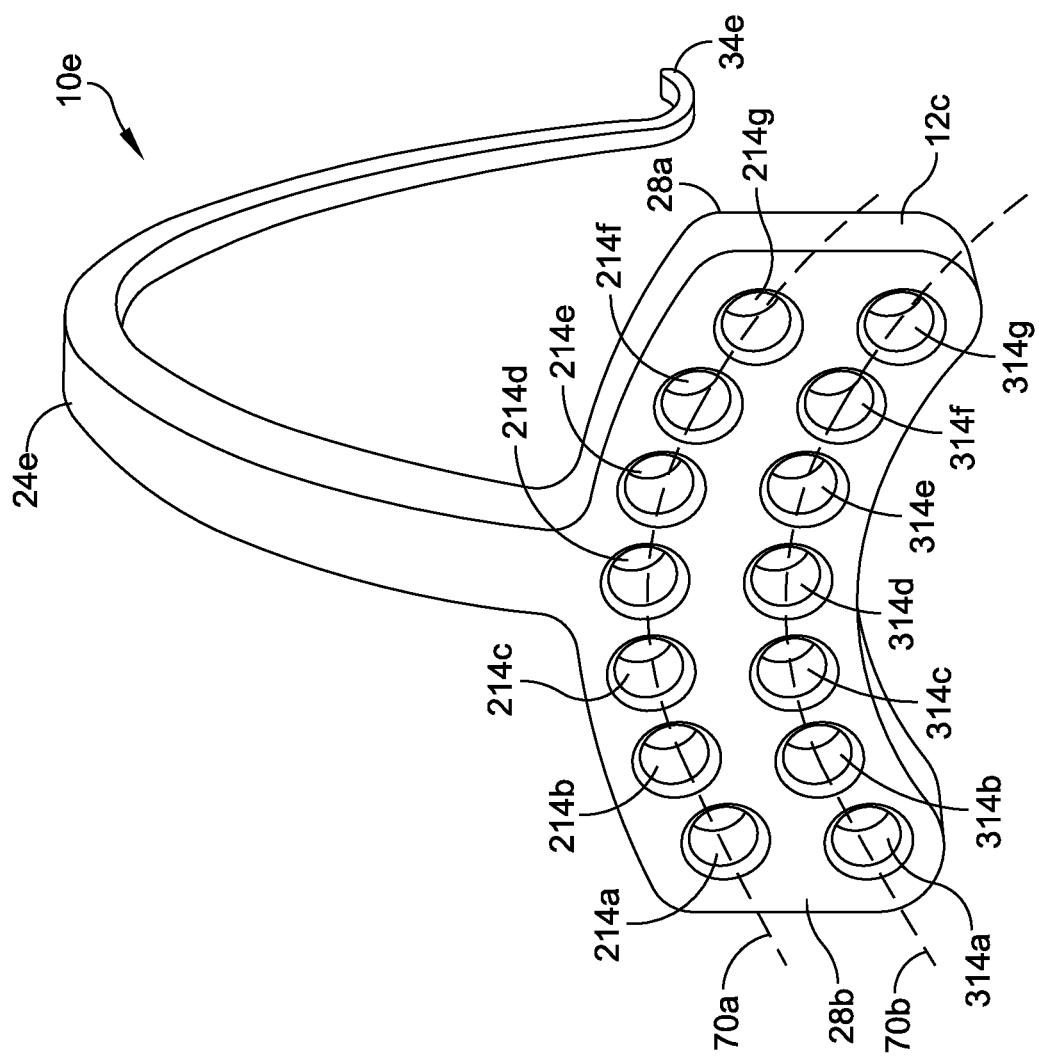
FIG. 17 illustrates a targeting guide having a first set of guide holes formed on a first arcuate axis of the body and a second set of guide holes formed on a second arcuate axis of the body, in accordance with some embodiments.

FIG. 17 illustrates a targeting guide 10e having a first set of guide holes 214a-214g on a first arcuate axis 70a of the body 12e and a second set of guide holes 314a-314g on a second arcuate axis 70b of the body 12e, in accordance with some embodiments. The targeting guide 10e is similar to the targeting guide 10d described in conjunction with FIG. 16, and similar description is not repeated herein. The guide holes 214a-214g, 314a-314g extend through the body 12e from a first surface 30a to a second surface 30b and are aligned along respective arcuate paths 70a, 70b extending from a first side 28a to a second side 28b of the body 12e. Each of the guide holes 214a-214g, 314a-314g is sized and configured to receive a guide sleeve (not shown) therethrough. The first set of guide holes 214a-214g and the second set of guide holes 314a-314g allows a user to select a position of one or more guide sleeves without adjusting a position of the targeting guide 10e. In the illustrated embodiment, the first arcuate axis 70a and the second arcuate axis 70b are substantially parallel, although it will be appreciated that the arcuate axes 70a, 70b can be non-parallel in some embodiments.

Figure 18:
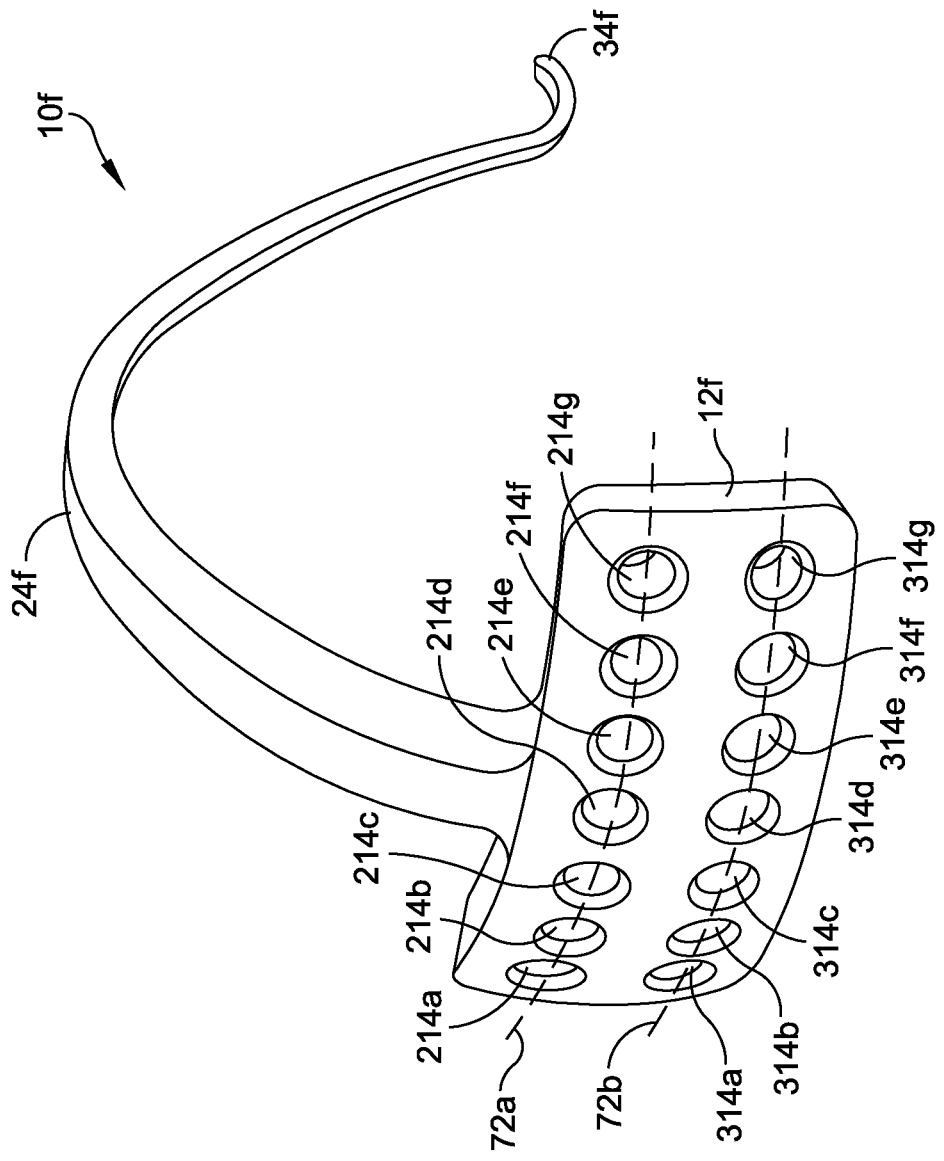
FIG. 18 illustrates a targeting guide having a first set of guide holes formed on a first horizontal axis of the body and a second set of guide holes formed on a second horizontal axis of the body, in accordance with some embodiments.

FIG. 18 illustrates a targeting guide 10f having a first set of guide holes 214a-214g on a first horizontal axis 72a and a second set of guide holes 314a-314g on a second horizontal axis 72b, in accordance with some embodiments. The targeting guide 10f is similar to the targeting guide 10e described in conjunction with FIG. 17, and similar description is not repeated herein. In the illustrated embodiment, the first horizontal axis 72a and the second horizontal axis 72b are substantially parallel, although it will be appreciated that the first and second horizontal axes 72a, 72b can be non-parallel. In some embodiments, the body 12e can have a curved and/or arcuate shape configured to conform to an outer surface of a patient.

Figure 19:
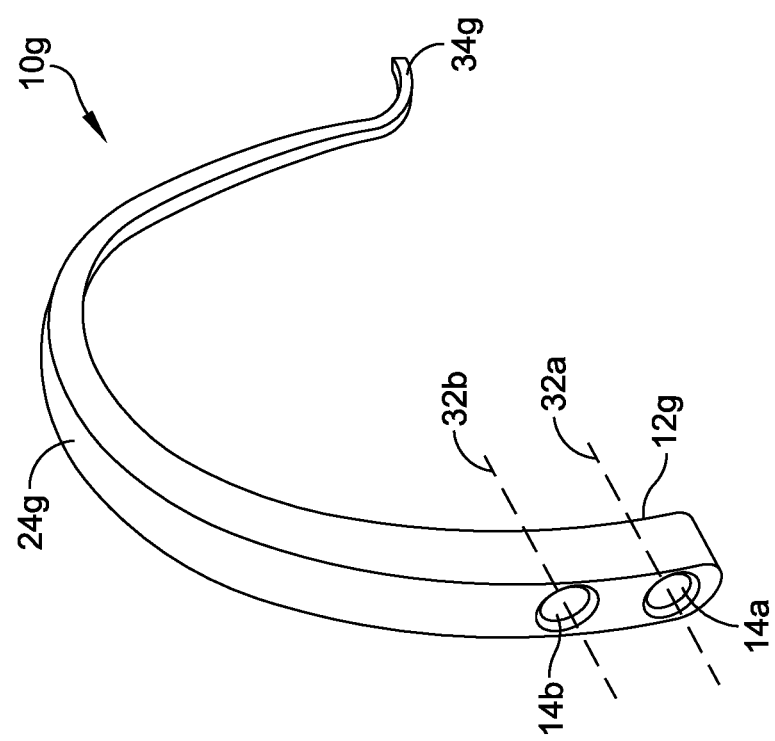
FIG. 19 illustrates a targeting guide having a continuous body and alignment arm, in accordance with some embodiments.

FIG. 19 illustrates a targeting guide 10g having a continuous body 12g and alignment arm 24g, in accordance with some embodiments. The targeting guide 10g is similar to the targeting guide 10 described in conjunction with FIGS. 1-9, and similar description is not repeated herein. The body 12g includes a first guide hole 14a and a second guide hole 14b extending therethrough. The body 12g and the alignment arm 24g extend continuously from a first end of the body 12g to a guide tip 34g. In some embodiments, the width and/or the thickness of the body 12g and/or the alignment arm 24g is tapered from the first end 28b to the guide tip 34g. For example, in the illustrated embodiment, the body 12g and the alignment arm 24g have a continuously tapered width and a continuously tapered thickness such that the body 12g is thickest and widest at the first end 28b and the alignment arm is thinnest at the guide tip 34g, although it will be appreciated that the body 12g and/or the alignment arm 24g can be tapered in any suitable dimension.

In some embodiments, the first guide hole 14a extends through the body 12g on a first axis 32a and the second guide hole 14b extends through the body 12g on a second axis 32b. In some embodiments, the first axis 32a and the second axis 32b are non-parallel. For example, in some embodiments, the first axis 32a and the second axis 32b are aligned such that the axes 32a, 32b intersect at a point corresponding to a predetermined portion of the guide tip 34g, such as the free end 38a. In other embodiments, the first axis 32a and the second axis 32b are aligned such that the axes 32a, 32b are non-intersecting along an expected path of a guide element inserted into a first bone portion 102a and a second bone portion 102b along the respective axis 32a, 32b.

Figure 20:
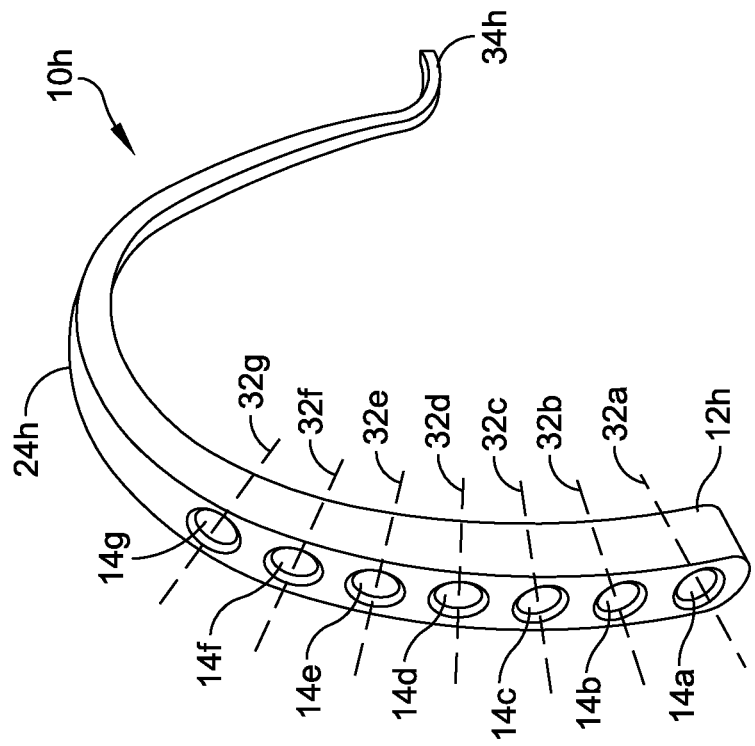
FIG. 20 illustrates a targeting guide having a continuous body and alignment arm including a plurality of guide holes formed therethrough, in accordance with some embodiments.

FIG. 20 illustrates a targeting guide 10h having a continuous body 12h and alignment arm 24h defining plurality of guide holes 14a-14g formed therethrough, in accordance with some embodiments. The targeting guide 10h is similar to the targeting guide 10g described in conjunction with FIG. 19, and similar description is not repeated herein. The targeting guide 10h includes a plurality of guide holes 14a-14g extending through the body 12g along respective hole axes 32a-32g. The hole axes 32a-32g define intersecting paths. In some embodiments, each of the hole axes 32a-32g intersect at a single point, such as a point corresponding to the guide tip 34h and/or the free end 40 of the guide tip 34h. In other embodiments, two or more of the hole axes 32a-32g can intersect at different points proximal to, aligned with, and/or distal to the guide tip 34h. The plurality of guide holes 14a-14g allow a user (such as a surgeon) to select multiple angles of approach for installing guide elements based on patient-specific anatomy and/or other operatively-determined information.

Figure 21:
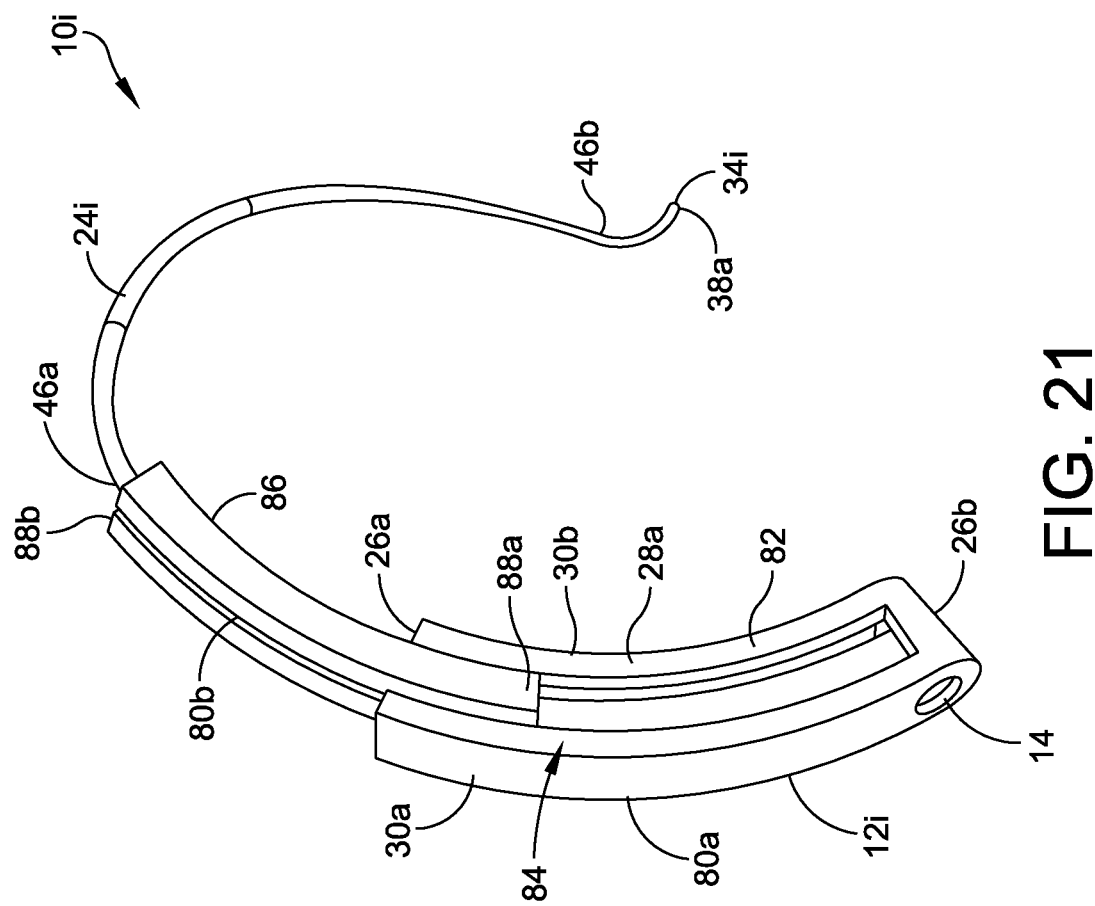
FIG. 21 illustrates a targeting guide having an adjustable body, in accordance with some embodiments.

FIG. 21 illustrates a targeting guide 10i having an adjustable alignment arm 24i, in accordance with some embodiments. The targeting guide 10i includes a body 12i having a first portion 80a and a second portion 80b. The first portion 80a includes a body 82 extending between an upper edge 26a and a lower edge 26b and between a first side 28a and a second side (not shown). The body 82 defines a first slot 84 formed in the first side 28a extending from an upper edge 26a into the body 12i. The slot 84 is sized and configured to the second portion 80b therein. In some embodiments, a second slot (not shown) is formed in the second side 28b extending from an upper edge 26a into the first portion 80a.

The first portion 80a defines a guide hole 14 extending from a first surface 30a to a second surface 30b. The guide hole 14 is sized and configured to receive a guide sleeve and/or a guide element therethrough. In some embodiments, the guide hole 14 is positioned adjacent to the lower edge 26b of the first portion 80a, although it will be appreciated that the guide hole 14 can be positioned through any suitable portion of the first portion 80a and/or the second portion 80b.

The body 12i further includes a second portion 80b extending from and slideable with respect to the first portion 80a. The second portion 80b includes an elongate, arcuate body 86 extending from a first end 88a to a second end 88b. The arcuate body 86 is sized and configured to be received within one or more of the slots 84 defined by the first portion 80a of the body 12i. For example, in the illustrated embodiment, the arcuate body 86 defines an I-beam shape having a first portion inserted into the slot 84 formed in the first portion 80a and a second portion extending beyond the slot 84. In other embodiments, the arcuate body 86 can have any suitable shape configured to be received within one or more slots 84 defined by the first portion 80a and/or be slideable with respect to the first portion 80a using any suitable mechanism.

An alignment arm 24i extends from the second end 88b of the second portion 80b of the body 12i. The alignment arm 24i extends along an arcuate path from a first end 46a to a second end 46b. In some embodiments, the alignment arm 24i is adjustable with respect to the second portion 80b of the body 12i. For example, in some embodiments, the second portion 80b of the body 12i defines a channel sized and configured to slideably receive a portion of the alignment arm 24i therein. The position of the alignment arm 24i (and the attached guide tip 34i) with respect to the second portion 80b of the body 12i can be adjusted by sliding the alignment arm 24i into and/or out of the second portion 80b of the body 12i. In other embodiments, the alignment arm 24i has a fixed relationship with the second portion 80b.

In use, the position of the guide tip 34i coupled to the alignment arm 24i is adjustable by sliding the second portion 80b within the first portion 80a and/or sliding the alignment arm 24i within the second portion 80b. The guide tip 34i can be deployed to a maximum deployment (as shown in FIG. 21). In this position, a portion of the guide tip 34i, such as a free end 38a, corresponds to an axis of the guide hole 14 formed through the first portion 80a of the body 12i.

In some embodiments, the arc of the body 12i and/or the alignment arm 24 are configured to maintain an alignment between the hole axis 32a of the guide hole 14 and the free end 40 of the guide tip 34i as the first portion 80a and the second portion 80b are slideably adjusted. For example, in some embodiments, as the overlap between the first portion 80a and the second portion 80b is increased (e.g., the body 12i is shortened), the arc of the body 12i maintains an alignment between the guide hole 14 and the free end 38a of the guide tip 34i. In other embodiments, the axis of the guide hole 14 and the free end 38a of the guide tip are aligned only when the second portion 80b of the body 12i is fully deployed from the first portion 80a.

Figure 22:
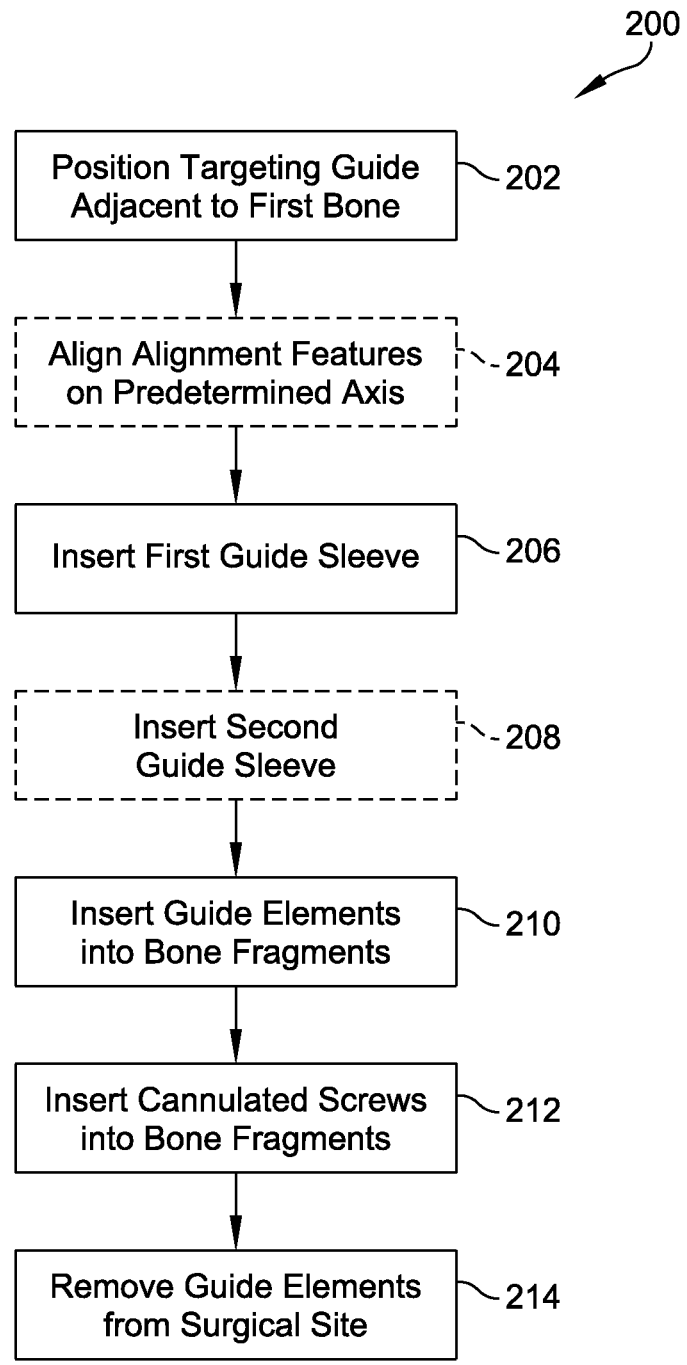
FIG. 22 is a flowchart illustrating a method of fixing a first bone fragment to a second bone fragment, in accordance with some embodiments.

FIG. 22 illustrates a method 200 of fixing a first bone fragment 102a to a second bone fragment 102b, in accordance with some embodiments. Although the method 200 is discussed herein using the targeting guide 10, it will be appreciated that the method 200 can utilize any of the targeting guides 10-10i discussed in conjunction with FIGS. 1-21, and is within the scope of this disclosure. At step 202, a targeting guide 10 is positioned adjacent to a first bone 102, The targeting guide 10 includes a body 12, an alignment arm 24 extending between a first end 42a coupled to the body and a second end 42b, and a tip 34 extending from the second end 42b of the alignment arm 24. The tip 34 includes a free end 38. The free end 38 of the tip 34 of the targeting guide 10 corresponds the exit position of a first guide element 110a and/or a second guide element 110b from a first bone fragment 102a when the first guide element 110a and/or the second guide element 110b are inserted through guide sleeves 116a, 116b coupled to the targeting guide 10, as discussed in greater detail below.

At optional step 204, alignment features (such as lateral alignment holes 46a, 46b and/or alignment protrusions 50a, 50b) of the targeting guide 10 are aligned on a predetermined axis. Alignment of the alignment features is configured to position the targeting guide 10 at a predetermined orientation and/or position with respect to one or more bone fragments 102a, 102b.

At step 206, a first guide sleeve 116a through a first guide hole 14a formed in the body 12. The first guide sleeve 116a defines a first channel extending therethrough. At step 206, a first guide element 110a is inserted through the channel of the first guide sleeve 116a and into the first bone 102. A portion of the tip 38 of the targeting guide 10 corresponds to an exit position of the first guide element 110a from the first bone 102.

At optional step 208, a second sleeve 116b is inserted through a second guide hole 14b formed in the body 10. The second guide sleeve 116b defines a second channel extending therethrough. The second channel is substantially parallel to the first channel of the first guide sleeve 116a after insertion of the first guide sleeve 116a and the second guide sleeve 116b into respective first guide hole 14a and second guide hole 14b.

At step 210, a first guide element 110a and/or a second guide element 110b are inserted through the channel of the respective first guide sleeve 116a and second guide sleeve 116b and into the first bone 102. The guide elements 110a, 110b extend through a first bone fragment 102a and into a second bone fragment 102b to maintain the first and second bone fragments 102a, 102b in respective predetermined positions. In some embodiments, the guide elements 110a, 110b can include a k-wire, although it will be appreciated that any suitable guide element can be used.

At step 212, the targeting guide 10 is removed from the surgical site and one or more cannulated screws 120a, 120b are coupled to the first bone. For example, a first cannulated screw 120a can be slideably positioned over the first guide element 110a and inserted through the first bone fragment 102a and the second bone fragment 102b and a second cannulated screw 120b can be slideably positioned over the second guide element 110b and inserted through the first bone fragment 102a and the second bone fragment 102b. The first and/or second cannulated screws 120a, 120b fix the relative positions of the first bone fragment 102a and the second bone fragment 102b. At step 214, the guide elements 110a, 110b are removed from the bone 102 after fixation of the bone by the fixation elements 120a, 120b.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A targeting guide, comprising:
a body defining a first guide hole, at least one alignment hole, and a channel, wherein the first guide hole is sized and configured to receive a guide sleeve therethrough, wherein the first guide hole extends through the body on a first axis, wherein the channel extends from an edge of the body into an interior portion of the body such that the channel intersects the first guide hole, wherein the at least one alignment hole is oriented parallel to the first guide hole and is positioned on the body such that, when an alignment device is disposed within the at least one alignment hole, the alignment device provides a visual indication of a trajectory of the first guide hole;
an alignment arm extending between a first end and a second end, wherein the first end is coupled to the body; and
a tip extending from the second end of the alignment arm, wherein the tip is aligned with the first axis of the first guide hole.

2. The targeting guide of claim 1, wherein the body defines a second guide hole extending through the body along a second axis.

3. The targeting guide of claim 2, wherein the first axis and the second axis are substantially parallel.

4. The targeting guide of claim 1, wherein the tip comprises a first portion extending from the second end of the alignment arm at a first angle and a second portion extending from the first portion at a second angle, and wherein the second portion is aligned with the first axis of the at least one hole.

5. The targeting guide of claim 1, wherein the at least one alignment hole is positioned laterally of the first guide hole.

6. The targeting guide of claim 1, wherein the alignment arm extends from the first end to the second end substantially along a horizontal axis.

7. The targeting guide of claim 1, wherein the alignment arm defines an arc extending from the first end to the second end.

8. The targeting guide of claim 1, comprising a first guide pin and a second guide pin extending from the body, wherein the first guide pin and the second guide pin are configured to indicate alignment of the targeting guide with respect to a bone.

9. A system, comprising:
a targeting guide, comprising:
a body defining a first guide hole, at least one alignment hole, and a channel, wherein the first guide hole extends through the body on a first axis, and wherein the channel extends from an edge of the body into an interior portion of the body such that the channel intersects the first guide hole, wherein the at least one alignment hole is oriented parallel to the first guide hole and is positioned on the body such that, when an alignment device is disposed within the at least one alignment hole, the alignment device provides a visual indication of a trajectory of the first guide hole;
an alignment arm extending between a first end and a second end, wherein the first end is coupled to the body; and
a tip extending from the second end of the alignment arm, wherein the tip is aligned with the first axis of the first guide hole;
a first guide sleeve sized and configured for insertion through the first guide hole, wherein the first guide sleeve defines a channel extending therethrough.

10. The system of claim 9, comprising a second guide sleeve sized and configured for insertion through a second guide hole defined by the body of the targeting guide, the second guide sleeve defining a channel extending therethrough.

11. The system of claim 10, wherein the channel of the first guide sleeve and the channel of the second guide sleeve are substantially parallel when the first and second guide sleeves are inserted into respective first and second guide holes.

12. The system of claim 9, wherein theat least one alignment hole is laterally aligned with the first guide hole.

13. The system of claim 9, wherein the body of the targeting guide includes a first guide pin and a second guide pin extending therefrom, wherein the first guide pin and the second guide pin are configured to indicate alignment of the targeting guide with respect to a selected reference point.

14. The targeting guide of claim 9, wherein the alignment arm extends from the first end to the second end substantially along a horizontal axis.

15. The targeting guide of claim 9, wherein the alignment arm defines an arc extending from the first end to the second end.

16. A method, comprising:
positioning a targeting guide adjacent to a first bone, wherein the targeting guide includes:
a body defining a first guide hole, at least one alignment hole, and a channel, the first guide hole extends through the body on a first axis, the channel extends from an edge of the body into an interior portion of the body such that the channel intersects the first guide hole, and the at least one alignment hole is oriented parallel to the first guide hole and is positioned on the body such that, when an alignment device is disposed within the at least one alignment hole, the alignment device provides a visual indication of a trajectory of the first guide hole;
an alignment arm extending between a first end coupled to the body and a second end, and a tip extending from the second end of the alignment arm and having a free end;

inserting a first guide sleeve through the first guide hole formed in the body;

inserting a first guide element through a channel defined by the first guide sleeve and into the first bone, wherein a portion of the tip of the targeting guide corresponds to an exit position of the first guide element from the first bone;

removing the first guide sleeve from the first guide hole; and removing the targeting guide from adjacent to the first bone by traversing the first guide element through the channel extending from an edge of the body into an interior portion of the body.

17. The method of claim 16, comprising inserting a first screw into the first bone, wherein the first screw is inserted over the first guide element.

18. The method of claim 16, wherein the free end of the tip of the targeting guide corresponds the exit position of the first guide element from a first bone fragment.

19. The method of claim 16, comprising:

inserting a second guide sleeve through a second guide hole formed in the body, wherein the second guide sleeve defines a second channel extending therethrough, and wherein the second channel of the second guide sleeve is substantially parallel with the first channel of the first guide sleeve after insertion of the first guide sleeve and the second guide sleeve into respective first guide hole and second guide hole; and inserting a second guide element through the channel of the second guide sleeve and into the first bone.

20. The method of claim 16, comprising:

inserting the alignment device into the at least one alignment hole; and aligning the alignment device with the first bone prior to insertion of the first sleeve into the first guide hole.

21. A system, comprising:

a targeting guide, comprising:

a body defining a guide hole, a channel, and an alignment hole, wherein the guide hole extends through the body on a first axis, wherein the channel extends from an edge of the body into an interior portion of the body such that the channel intersects the first guide hole, and wherein the alignment hole extends through the body on a second axis substantially parallel with the first axis;

an alignment arm extending between a first end and a second end, wherein the first end is coupled to the body; and a tip extending from the second end of the alignment arm, wherein the tip is aligned with the first axis of the first guide hole; and an alignment device selected from the group consisting of a cannulated screw, a k-wire, and a guide pin, wherein the alignment device is configured for insertion through the alignment hole, wherein the alignment hole is positioned on the body such that, when the alignment device is disposed within the alignment hole, the alignment device provides a visual indication of a trajectory of the first guide hole.

\* \* \* \* \*